(12) United States Patent
Dadhwal

(10) Patent No.: US 11,407,992 B2
(45) Date of Patent: Aug. 9, 2022

(54) METHODS OF DETERMINING A SURGICAL MARGIN AND METHODS OF USE THEREOF

(71) Applicant: 10x Genomics, Inc., Pleasanton, CA (US)

(72) Inventor: Smritee Dadhwal, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/549,175

(22) Filed: Dec. 13, 2021

(65) Prior Publication Data

US 2022/0098576 A1   Mar. 31, 2022

Related U.S. Application Data

(63) Continuation of application No. PCT/US2021/036415, filed on Jun. 8, 2021.

(60) Provisional application No. 63/036,195, filed on Jun. 8, 2020.

(51) Int. Cl.
| | | |
|---|---|---|
| *C12N 15/10* | (2006.01) | |
| *C12Q 1/6874* | (2018.01) | |
| *C12Q 1/6841* | (2018.01) | |

(52) U.S. Cl.
CPC ....... *C12N 15/1065* (2013.01); *C12Q 1/6841* (2013.01); *C12Q 1/6874* (2013.01)

(58) Field of Classification Search
CPC . C12N 15/1065; C12Q 1/6874; C12Q 1/6841
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Homes |
| 5,512,462 A | 4/1996 | Cheng |
| 5,582,977 A | 12/1996 | Yue |

(Continued)

FOREIGN PATENT DOCUMENTS

| | | |
|---|---|---|
| CN | 1680604 | 10/2005 |
| CN | 101221182 | 7/2008 |

(Continued)

OTHER PUBLICATIONS

U.S. Appl. No. 60/416,118, filed Oct. 3, 2002, Fan et al.

(Continued)

*Primary Examiner* — Jeremy C Flinders
*Assistant Examiner* — Taryn Kimberly Wood
(74) *Attorney, Agent, or Firm* — Fish & Richardson P.C.

(57) ABSTRACT

Provided herein are methods of determining a surgical margin and the site and size of a tissue to be resected from a subject, and methods of use thereof.

28 Claims, 4 Drawing Sheets

(56) References Cited

U.S. PATENT DOCUMENTS

| | | |
|---|---|---|
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Famqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,573,043 B1 | 6/2003 | Coben et al. |
| 6,579,695 B1 | 6/2003 | Lambalot |
| 6,620,584 B1 | 9/2003 | Chee |
| 6,632,641 B1 | 10/2003 | Brennan |
| 6,699,710 B1 | 3/2004 | Kononen |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,878,515 B1 | 4/2005 | Landegren |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 6,969,589 B2 | 11/2005 | Patil |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,128,893 B2 | 10/2006 | Leamon et al. |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,595,883 B1 | 9/2009 | El Gamal |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,700,286 B2 | 4/2010 | Stroun et al. |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,288,103 B2 | 10/2012 | Oliphant |
| 8,337,851 B2 | 12/2012 | Aukerman |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,507,204 B2 | 8/2013 | Pierce et al. |
| 8,551,710 B2 | 10/2013 | Bernitz et al. |
| 8,568,979 B2 | 10/2013 | Stuelpnagel et al. |
| RE44,596 E | 11/2013 | Stroun et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,748,103 B2 | 6/2014 | Faham et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 9,005,891 B2 | 4/2015 | Sinicropi et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,085,798 B2 | 7/2015 | Chee |
| 9,121,069 B2 | 9/2015 | Lo |
| 9,194,001 B2 | 11/2015 | Brenner |
| 9,217,176 B2 | 12/2015 | Faham |

(56) References Cited

U.S. PATENT DOCUMENTS

| | | |
|---|---|---|
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,340,830 B2 | 5/2016 | Lipson |
| 9,371,598 B2 | 6/2016 | Chee |
| 9,376,716 B2 | 6/2016 | Van Eijk |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,512,487 B2 | 12/2016 | Faham et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,049,770 B2 | 8/2018 | Madabhushi et al. |
| 10,059,989 B2 | 8/2018 | Giresi et al. |
| 10,059,990 B2 | 8/2018 | Boyden et al. |
| 10,078,895 B2 | 9/2018 | Madabhushi et al. |
| 10,095,832 B2 | 10/2018 | Van Eijk |
| 10,144,966 B2 | 12/2018 | Cantor |
| 10,196,691 B2 | 2/2019 | Harkin et al. |
| 10,208,982 B2 | 2/2019 | Bannish et al. |
| 10,221,461 B2 | 3/2019 | Robins et al. |
| 10,246,752 B2 | 4/2019 | Faham et al. |
| 10,273,541 B2 | 4/2019 | Hindson et al. |
| 10,308,982 B2 | 6/2019 | Chee |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 2001/0055764 A1 | 12/2001 | Empendocles et al. |
| 2002/0006477 A1 | 1/2002 | Shishido et al. |
| 2002/0040275 A1 | 4/2002 | Cravatt |
| 2002/0055100 A1 | 5/2002 | Kawashima |
| 2002/0086441 A1 | 7/2002 | Baranov et al. |
| 2002/0132246 A1 | 9/2002 | Kallioniemi et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0170637 A1 | 9/2003 | Pirrung et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0002090 A1 | 1/2004 | Mayer et al. |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0019776 A1 | 1/2005 | Callow et al. |
| 2005/0026188 A1 | 2/2005 | Van Kessel |
| 2005/0037362 A1 | 2/2005 | Remacle et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0196786 A1 | 9/2005 | Levy |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0105352 A1 | 5/2006 | Qiao et al. |
| 2006/0110739 A1 | 5/2006 | Heyduk |
| 2006/0188875 A1 | 8/2006 | Cox et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0228758 A1 | 10/2006 | Muchhal et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0161029 A1 | 7/2007 | Li et al. |
| 2007/0166705 A1 | 7/2007 | Milton et al. |
| 2007/0172873 A1 | 7/2007 | Brenner et al. |
| 2007/0178503 A1 | 8/2007 | Jiang |
| 2007/0207482 A1 | 9/2007 | Church et al. |

(56) References Cited

U.S. PATENT DOCUMENTS

| | | |
|---|---|---|
| 2007/0251824 A1 | 11/2007 | Patton |
| 2007/0254305 A1 | 11/2007 | Paik et al. |
| 2007/0269805 A1 | 11/2007 | Hogers |
| 2007/0280517 A1 | 12/2007 | De La Torre-Bueno et al. |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0153086 A1 | 6/2008 | Wong |
| 2008/0160580 A1 | 7/2008 | Adessi et al. |
| 2008/0199929 A1 | 8/2008 | Yeung et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0197326 A1 | 8/2009 | El Gamal et al. |
| 2009/0215633 A1 | 8/2009 | van Eijk et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0289184 A1 | 11/2009 | Deininger |
| 2009/0291854 A1 | 11/2009 | Weisinger-Mayr et al. |
| 2009/0305237 A1 | 12/2009 | Cantor et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0064630 A1 | 3/2011 | Coulling et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0275077 A1 | 11/2011 | James |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0245053 A1 | 9/2012 | Shirai et al. |
| 2012/0258871 A1 | 10/2012 | Kozlov et al. |
| 2012/0289414 A1 | 11/2012 | Mitra et al. |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0079232 A1 | 3/2013 | Kain et al. |
| 2013/0122516 A1 | 5/2013 | Meares |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0080715 A1 | 3/2014 | Lo et al. |
| 2014/0121118 A1 | 5/2014 | Warner |
| 2014/0155274 A1 | 6/2014 | Xie et al. |
| 2014/0274731 A1 | 9/2014 | Raymond et al. |
| 2014/0296081 A1 | 10/2014 | Diehn et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2015/0051085 A1 | 2/2015 | Vogelstein et al. |
| 2015/0072867 A1 | 3/2015 | Soldatov |
| 2015/0148239 A1 | 5/2015 | Jon |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0016909 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0275669 A1 | 9/2017 | Weissleder et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0112209 A1 | 4/2018 | Eshoo |
| 2018/0112261 A1 | 4/2018 | Van Driel et al. |
| 2018/0156784 A1 | 6/2018 | Usmani et al. |
| 2018/0163265 A1 | 6/2018 | Zhang et al. |
| 2018/0179591 A1 | 6/2018 | van Eijk |
| 2018/0180601 A1 | 6/2018 | Pedersen et al. |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0312822 A1 | 11/2018 | Lee et al. |
| 2019/0017106 A1 | 1/2019 | Frisen et al. |
| 2019/0024153 A1 | 1/2019 | Frisen et al. |
| 2019/0024154 A1 | 1/2019 | Frisen et al. |
| 2019/0055594 A1 | 2/2019 | Samusik et al. |
| 2019/0085383 A1 | 3/2019 | Church et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0249248 A1 | 8/2019 | Beechem et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |

(56) References Cited

U.S. PATENT DOCUMENTS

| | | |
|---|---|---|
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0367969 A1 | 12/2019 | Belhocine et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uylingco et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |

FOREIGN PATENT DOCUMENTS

| | | |
|---|---|---|
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 2350648 | 7/2017 |
| EP | 3511423 | 7/2019 |
| EP | 3541956 | 9/2019 |
| JP | 2007-014297 | 1/2007 |
| JP | 2007-074967 | 3/2007 |
| JP | 2009-036694 | 2/2009 |
| RU | 2145635 | 2/2000 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2001/06012 | 1/2001 |
| WO | WO 2001/007915 | 2/2001 |
| WO | WO 2001/009363 | 2/2001 |
| WO | WO 2001/042796 | 6/2001 |
| WO | WO 2001/090415 | 11/2001 |
| WO | WO 2001/096608 | 12/2001 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/055159 | 7/2004 |
| WO | WO 2004/067759 | 8/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/13 9766 | 12/2007 |
| WO | WO 2007/145612 | 12/2007 |
| WO | WO 2008/069906 | 6/2008 |
| WO | WO 2009/032167 | 3/2009 |
| WO | WO 2009/152928 | 12/2009 |
| WO | WO 2009/156725 | 12/2009 |
| WO | WO 2010/019826 | 2/2010 |

(56) References Cited

FOREIGN PATENT DOCUMENTS

| | | |
|---|---|---|
| WO | WO 2010/027870 | 3/2010 |
| WO | WO 2010/126614 | 11/2010 |
| WO | WO2011/008502 | 1/2011 |
| WO | WO 2011/062933 | 5/2011 |
| WO | WO 2011/068088 | 6/2011 |
| WO | WO 2011/127099 | 10/2011 |
| WO | WO 2012/049316 | 4/2012 |
| WO | WO 2012/071428 | 5/2012 |
| WO | WO 2012/129242 | 9/2012 |
| WO | WO 2012/140224 | 10/2012 |
| WO | WO 2012/159089 | 11/2012 |
| WO | WO 2012/168003 | 12/2012 |
| WO | WO 2013/123442 | 8/2013 |
| WO | WO 2013/138510 | 9/2013 |
| WO | WO 2013/142389 | 9/2013 |
| WO | WO 2013/150083 | 10/2013 |
| WO | WO 2014/044724 | 3/2014 |
| WO | WO 2014/060483 | 4/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/161173 | 10/2015 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/119320 | 6/2021 |
| WO | WO 2021/133849 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2.02.2/060953 | 3/2022 |
| WO | WO 2022/060798 | 3/2022 |
| WO | WO 2022/087273 | 4/2022 |
| WO | WO 2022/098810 | 5/2022 |
| WO | WO 2022/099037 | 5/2022 |

OTHER PUBLICATIONS

U.S. Appl. No. 61/267,363, filed Dec. 7, 2009, Fan et al.
U.S. Appl. No. 61/839,313, filed Jun. 25, 2013, Chee et al.
U.S. Appl. No. 61/839,320, filed Jun. 25, 2013, Chee et al.
U.S. Appl. No. 61/902,105, filed Nov. 8, 2013, Kozlov et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Aflymetrix Part No. 90094 (Aflymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrNOcH17rEkOUXwdl9It/e54d99fb08a8fl500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEkOUXwdl9It/e54d99fb08a8fl500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpdlbFVha1pexR/8baa08d9007157592b65b2cdc7130990/CG000239_VisiumSpatialGeneExpression_UserGuide_RevD.pdf>, 70 pages.

(56) References Cited

OTHER PUBLICATIONS

Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Aflymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Aflymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amgad et al., "Report on computational assessment of Tumor Infiltrating Lymphocytes from the International Immuno-Oncology Biomarker Working Group," Nature Partner Journals Breast Cancer, May 2020, 6:16, 13 pages.
Andresen et al., "Deciphering the Antibodyome—Peptide Arrays for Senim Antibody Biomarker Diagnostics," Current Proteomics, 6(1):1-12, 2009.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Asp et al., "Spatial detection of fetal marker genes expressed at low level in adult human heart tissue," Scientific Reports, 2017, 7(1):12941, 10 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profdes histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bielas et al., "Human cancers express a mutator phenotype," Proc. Natl. Acad. Sci. USA, 2006, 103(48): 18238-18242.
Biosyntagma.Com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Bimey et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blandini et al., "Animal models of Parkinson's disease," FEBS J., Apr. 2012, 279(7): 1156-66.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buemostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem, J, 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Cerutti et al., "Generation of sequence-specific, high affinity anti-DNA antibodies," Journal of Biological Chemistiy, 2001, 276(16):12769-12773.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatteijee et al., "Mitochondrial DNA mutations in human cancer. Oncogene," 2006, 25(34):4663-4674.
Chen et al., "A Homogeneous, Ligase-mediated DNA diagnostic test," Genome research, 1998, 8(5):549-556.
Chen et al., "DNA hybridization detection in a microfluidic Channel using two fluorescently labelled nucleic acid probes," Biosensors and Bioelectronics, 2008, 23(12):1878-1882.
Chen et al., "Expansionmicroscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.

(56) References Cited

OTHER PUBLICATIONS

Chrisey et al., "Covalent attachment of synthetic DNA to self-assembled monolayer films," Nucleic Acids Res., Aug. 1996, 24(15):3031-9.
Co et al., "Factors affecting the under-diagnosis of atypical ductal hyperplasia diagnosed by core needle biopsies—A 10-year retrospective study and review of the literature," Int J Surg., Jan. 2018, 49:27-31.
Constantine et al., "Use of genechip high-density oligonucleotide arrays for gene expression monitoring," Life Sceience News, Amersham Life Science, 1998, pp. 11-14.
Copeland et al., "Mitochondrial DNA Alterations in Cancer," Cancer Invest., 2002, 557-569.
Corces et al., "An improved ATAC-seq protocol reduces background and enables interrogation of frozen tissues," Nat. Methods, 2017, 14(10):959-962.
Cornett et al., "MALDI imaging mass spectrometry: molecular snapshots of biochemical systems," Nature Methods, 2007, 4(10):828-833.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistiy and Biology, 2002, 9(2):253-264.
Czamik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dawson et al., "Animal models of neurodegenerative diseases," Nat Neurosci., Oct. 2018, 21(10):1370-1379.
Dawson et al., "Genetic animal models of Parkinson's disease," Neuron, Jun. 2010, 66(5):646-661.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "Accurate sequencing by hybridization for DNA diagnostics and individual genomics," Nature Biotechnology, 16:54-58, 1998.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem,, 1988, 169(1):104-108.
Eagen, "Principles of Chromosome Architecture Revealed by Hi-C," Trends in Biochemical Sciences, Jun. 2018, 43(6):469-478.
Eberwine, "Amplification of mRNA populations using aRNA generated from immobilized oligo(dT)-T7 primed cDNA," BioTechniques, 1996, 20(4):584-91.

Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Emmert-Buck et al., "Laser capture microdissection," Science, Nov. 1996, 274(5289):998-1001.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fluidigm, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
Fluidigm, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.
Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.
Fluidigm, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://

(56) References Cited

OTHER PUBLICATIONS web.archive.org/web/20150214084616/http://genearrays.com/services/microarrays/illumina/beadarray-technology/>, [retrieved on Jan. 30, 2020], 3 pages.
Giacomello et al., "Spatially resolved transcriptome profiling in model plant species", Nature Plants 3, 17061, 11 pages, 2017.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goltsev et al., "Deep Profiling of Mouse Splenic Architecture with CODEX Multiplexed Imaging", Cell, 2018, 174(4):968-981.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, p. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hadley et al., "Determining composition of micron-scale protein deposits in neurodegenerative disease by spatially targeted optical microproteomics," ELIFE, 2015, 4(e09579):21 pages.
Hahnke et al., "Striptease on glass: validation of an improved stripping procedure for in situ microarrays," J Biotechnol., Jan. 2007, 128(1):1-13.
Han et al., "3C and 3C-based techniques: the powerful tools for spatial genome organization deciphering", Molecular Cytogenetics (2018) 11: 21, 10 pages, 2018.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hlubek et al., "Heterogeneous expression of Wnt/b-catenin target genes within colorectal cancer," 2007, Int. J. Cancer: 2017, 1941-1948.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "High reproducibility using sodium hydroxide-stripped long oligonucleotide DNA microarrays," Biotechniques, Jan. 2005, 38(1):121-4.
Hycultbiotech.Com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Inoue and Wittbrodt, "One for All—A Highly Efficient and Versatile Method for Fluorescent Immuno staining in Fish Embryos," PLoS One 6, e19713, 2011.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistiy, Aug. 3, 2015, 7(9):752-758.
Kashyap et al., "Selective local lysis and sampling of live cells for nucleic acid analysis using a microfluidic probe," Sci Rep., Jul. 2016, 6:29579, 10 pages.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistiy, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of Mycobacterium avium: Tn552 to the rescue," Mol Microbiol., Jan. 2002, 43(1)473-86.
Kleckner et al., "Tn10 and IS10 transposition and chromosome rearrangements: mechanism and regulation in vivo and in vitro," Curr Top Microbiol Immunol., 1996, 20449-82.
Kolovos et al., "Investigation of the spatial structure and interactions of the genome at sub-kilobasepair resolution using T2C," Nat. Protoc. 13, 459-477, 2018.
Korbel et al., "Paired-end mapping reveals extensive structural variation in the human genome," Science, 2007, 318(5849)420-426.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmcogenomics, Febmary 2000, 1(1):95-100.
Lage et al., "Whole genome analysis of genetic alterations in small DNA samples using hyperbranched strand displacement amplification and array-CGH," Genome Research, 2003, 13(2):294-307.

(56) References Cited

OTHER PUBLICATIONS

Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Larman et al., "Sensitive, multiplex and direct quantification of RNA sequences using a modified RASL assay," Nucleic Acids Research, 2014, 42(14):9146-9157.
Lassmann et al., A Novel Approach For Reliable Microarray Analysis of Microdissected Tumor Cells From Formalin-Fixed and Paraffin-Embedded Colorectal Cancer Resection Specimens, J Mol Med, 87, 211-224, 2009.
Lee et al., "Fluorescent in situ sequencing (FISSEQ) of RNA for gene expression profiling in intact cells and tissues," Nature Protocols, 2015, 10(3)442-458.
Lee et al., "Improving the efficiency of genomic loci capture using oligonucleotide arrays for high throughput resequencing," BMC Genomics, Dec. 2009, 10:646, 12 pages.
Lein et al., "The promise of spatial transcriptomics for neuroscience in the era of molecular cell typing", Science 358, 64-69, 2017.
Leriche et al., "Cleavable linkers in chemical biology," Bioorganic & Medicinal Chemistry, 2012, 20:571-582.
Lewczuk et al., "Cerebrospinal fluid and blood biomarkers for neurodegenerative dementias: An update of the Consensus of the Task Force on Biological Markers in Psychiatry of the World Federation of Societies of Biological Psychiatry," World J Biol Psychiatry, Jun. 2018, 19(4):244-328.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet, 1998, 19(3):225-232.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.

Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyck et al., "Immunohistochemical markers for quantitative studies of neurons and glia in human neocortex," J Histochem Cytochem, 2008, 56(3):201-21.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Maniatis et al., "Spatiotemporal Dynamics of Molecular Pathology in Amyotrophic Lateral Sclerosis", 54 pages, 2018.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
McKernan et al., "Sequence and structural variation in a human genome uncovered by short-read, massively parallel ligation sequencing using two-base encoding," Genome Res., 19: 1527-41, 2009.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans- chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3 A," Gene, 1982, 20(3):317-322.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Motea et al., "Terminal deoxynucleotidyl transferase: the story of a misguided DNA polymerase," Biochim Biophys Acta., May 2010, 1804(5):1151-66.
Nagahara et al., "Neuroprotective effects of brain-derived neurotrophic factor in rodent and primate models of Alzheimer's disease," Nat Med., Mar. 2009, 15(3):331-337.
Nandakumar et al., "How an RNA Ligase Discriminates RNA versus DNA Damage," Molecular Cell, 2004, 16:211-221.
Nanostring, "GeoMx—nCounter DSP Instrument User Manual," MAN-10088-05 for software v2.1, Nov. 2020, 106 pages.
Nanostring, "GeoMx—NGS DSP Instrument User Manual," MAN-10116-03 for software v2.1, Dec. 2020, 104 pages.
Ncbi.nlm.nih.gov, [online], "Molecular Inversion Probe Assay," available on or before Oct. 14, 2014, via Internet Archive: Wayback Machine URL<https://web.archive.org/web/20141014124037/https://

(56) References Cited

OTHER PUBLICATIONS www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitoiy action of Ap5A," FEBS Lett., Mar. 1987, 213(1):204-8.
Park et al., "Single cell trapping in larger micro wells capable of supporting cell spreading and proliferation," Microfluid Nanofluid, 2010, 8:263-268.
Park et al., "The Estimation of Breast Cancer Disease-Probability by Difference of Individual Susceptibility," Cancer Res. Treat, Feb. 2003, 35(1):35-51, Abstract.
Paterson et al., "Cerebrospinal fluid in the differential diagnosis of Alzheimer's disease: clinical utility of an extended panel of bio markers in a specialist cognitive clinic," Alzheimers Res Then, Mar. 2018, 10(1):32, 11 pages.
PCT International Search Report and Written Opinion in International Appln. No. PCT/US2021/036415, dated Sep. 14, 2021, 14 pages.
Pellestor et al., "The peptide nucleic acids (PNAs), powerful tools for molecular genetics and cytogenetics," Eur J Hum Genet, Sep. 2004, 12(9):694-700.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Tn5 transposase and tagmentation procedures for massively scaled sequencing projects," Genome Res., Dec. 2014, 24(12):2033-40.
Pilewskie et al., "Margins in breast cancer: How much is enough?," Cancer, Apr. 2018, 124(7):1335-1341.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raab et al., "Human tRNA genes function as chromatin insulators," EMBO J., Jan. 2012, 31(2):330-50.
Rajeswari et al., "Multiple pathogen biomarker detection using an encoded bead array in droplet PCR," J. Microbial Methods, Aug. 2017, 139:22-28.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistiy, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Rubin et al., "Whole-genome resequencing reveals loci under selection during chicken domestication.," Nature, Mar. 2010, 464: 587-591.
Salem et al., "Multidimensional transcriptomics provides detailed information about immune cell distribution and identity in HER2+ breast tumors", bioRxiv, 41 pages, 2018.
Salmeén et al., "Barcoded solid-phase RNA capture for Spatial Transcriptomics profding in mammalian tissue sections," Nature Protocols, Oct. 2018, 13(11):2501-2534.
Saxonov et al.,"10x Genomics, Mastering Biology to Advance Human Health," PowerPoint, 10x, 2020, 41 pages.
Scheideler et al., "Recapitulating complex biological signaling environments using a multiplexed, DNA-patterning approach," Sci. Adv., 2020, 6:eay5696.
Schena et al., "Quantitative monitoring of gene expression patterns with a complementary DNA microarray," Science, Oct. 1995, 270(5235):467-470.
Schmitt et al., "Detection of ultra-rare mutations by next-generation sequencing," PNAS (2012) 109:14508-14523.
Schweitzer et al., "Multiplexed protein profding on microarrays by rolling-circle amplification," Nature Biotechnology, Apr. 2002, 20(4):359-365.
Segaliny et al., "Functional TCR T cell screening using single-cell droplet microfluidics†," Lab Chip, 2018, 3733-3749.
Sergeeva et al., "Display technologies: Application for the discovery of drug and gene delivery agents," Advanced Drug Delivery Reviews, 2006, 58(15):1622-1654.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Sheth et al., "Spatial metagenomic characterization of microbial biogeography in the gut," Nature Biotechnology, Aug. 2019, 37:877-883.
Shi, "Enabling large-scale pharmacogenetic studies by high-throughput mutation detection and genotyping technologies," Clin. Chem., Feb. 2001, 47(2):164-172.
Shoemaker et al., "Quantitative phenotypic analysis of yeast deletion mutants using a highly parallel molecular bar-coding strategy," Nature genetics (1996) 14:450-456.

(56) References Cited

OTHER PUBLICATIONS

Sievertzon et al., "Transcriptome analysis in primary neural stem cells using a tag cDNA amplification method," BMC Neuroscience, Dec. 2005, 6: 28.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA,, May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tegtmeyer et al., "Alternative Interactions of the SV40 A Protein with DNA," Virology, 1981, 115:75-87.
Tentori et al., "Detection of Isoforms Differing by a Single Charge Unit in Individual Cells," Chem. Int. Ed., 2016, 55(40):12431-5.
Thiery et al., "Multiplex target protein imaging in tissue sections by mass spectrometry—TAMSIM," Rapid Commun, Mass Spectrom., 2007, 21:823-829.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toss et al., "Breast conservation in ductal carcinoma in situ (DCIS): what defines optimal margins?," Histopathology, Apr. 2017, 70(5):681-692.
Trejo et al., "Extraction-free whole transcriptome gene expression analysis of FFPE sections and histology-directed subareas of tissue," PLoS ONE, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandemoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.

Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Wade et al., "Genome sequence, comparative analysis, and population genetics of the domestic horse.," Science., 326: 865-7, 2009.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Waxman et al., "De-regulation of common housekeeping genes in hepatocellular carcinoma," BMC Genomics, 2007, 1-9.
Weimeich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Willi-Monnerat et al., "Comprehensive spatiotemporal transcriptomic analyses of the ganglionic eminences demonstrate the uniqueness of its caudal subdivision," Molecular and Cellular Nueorsciences 37: 845-856, 2008.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Xiao et al., "Direct determination of haplotypes from single DNA molecules," Nature Methods, 2009, 6(3):199-01.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Yoda et al., "Site-specific gene expression analysis using an automated tissue micro-dissection punching system," Sci Rep., Jun. 2017, 7(1):4325, 11 pages.
Yoosuf et al., "Identification and transfer of spatial transcriptomics signatures for cancer diagnosis," Breast Cancer Res., Jan. 2020, 22(1):6, 10 pages.

(56) References Cited

OTHER PUBLICATIONS

Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes\," Chem. Commun., 2013, 49:10013-10015.
Zhang et al., "Single-base mutational analysis of cancer and genetic diseases using membrane bound modified oligonucleotides," Nucleic Acids Res., Jul. 1991, 19(14):3929-33.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sip and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Zilberman et al., "Genome-wide analysis of DNA methylation patterns," Development (2007) 134: 3959-3965.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine, 2013 11(104):1-7.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61ef6388a72564eeb96bc294967/CG000238_VisiumSpatialTissueOptimizationUserGuide_Rev_A.pdf>, 46 pages.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Cruz el al.. "Methylation in cell-free DNA for early cancer detection," Annm Oncol., Jun. 2018, 29(6):1351-1353.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Ke et al., "In situ sequencing for RNA analysis in preserved tissue and cells," Nat Methods., Sep. 2013, Supplementary Materials, 29 pages.
Miner et al., "Molecular barcodes detect redundancy and contamination in hairpin-bisulfite PCR," Nucleic Acids Res., Sep. 2004, 32(17):e135, 4 pages.
Wang et al., "Tagmentation-based whole-genome bisulfite sequencing," Nature Protocols, Oct. 2013, 8(10):2022-2032.
Anacyte.com [online], "CellCover," 2022, retrieved on May 23, 2022, retrieved from URL<https://www.anacyte.com/>, 15 pages.
Asp et al., "Spatially Resolved Transcriptomes—Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenstrable et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Biolegend.com [online], "Microscopy," 2022, retrieved on May 23, 2022, retrieved from URL<https://www.bioiegend.com/en-us/microscopy#applications-fivecolorfluorescencemiscroscopy>, 4 pages.

Blair et al., "Microarray temperature optimization using hybridization kinetics," Methods Mol Biol., 2009, 529:171-96.
Bolotin et al., "MiXCR: software tor comprehensive adaptive immunity profiling," Nat Methods., May 2015, 12(5):380-1.
Chen et al., "Parallel single nucleotide polymorphism genotyping by surface invasive cleavage with universal detection," Anal Chem., Apr. 2005. 77(8):2400-5.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Ciaccio et al.. "Systems analysis of EGF receptor signaling dynamics with microwestern arrays," Nat Methods, Feb. 2010, 7(2):148-55.
Espina et al., "Laser-capture microdissection," Nat Protoc, 2006, 1(2):586-603.
Gerard et al., "Excess dNTPs minimize RNA hydrolysis during reverse transcription," Biotechniques, Nov. 2002, 33(5):984, 986, 988, 990.
Hessner et al., "Genotyping of factor V G1691A (Leiden) without the use of PCR by invasive cleavage of oligonucleotide probes," Clin Chem., Aug. 2000. 46(8 Pt 1):1051-6.
Hoffman et al., "Formaldehyde crosslinking: a tool for the study of chromatin complexes," J Biol Chem., Oct. 2015, 290(44):26404-11.
Hughes et al., "Microfluidic Western blotting," PNAS, Dec. 2012, 109(52):21450-21455.
Illumina.com [online], "Ribo-Zero® rRNA Removal Kit Reference Guide," Aug. 2016, retrieved on Apr. 26. 2022. retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity7," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by cblorella virus DNA ligase and a novel iLock assay with improved direct RNA detection accuracy," Nucleic Acids Research, Oct. 2017, 45(18):e161, 9 pages.
Lou et al., "A review of room temperature storage of biospecimen tissue and nucleic acids for anatomic pathology laboratories and biorepositories," Clin Biochem., Mar. 2014, 47(4-5):267-73.
Lyamichev et al., "Invader assay for SNP genotyping," Methods Mol Biol., 2003, 212:229-40.
Lvamichev et al., "Polymorphism identification and quantitative detection of genomic DNA by invasive cleavage of oligonucleotide probes," Nat Biotechnol., Mar. 1999, 17(3):292-6.
Lykidis et al., "Novel zinc-based fixative for high quality DNA, RNA and protein analysis." Nucleic Acids Res., Jun. 2007, 35(12):e85, 10 pages.
Madissoon et al., "scRNA-seq assessment of the human lung, spleen, and esophagus tissue stability after cold preservation," Genome Biol., Dec. 2019, 21(1):1, 16 pages.
Nadji et af. "Immunohistochemistry of tissue prepared by a molecular-friendlv fixation and processing system," Appl Immunohistochem Mol Morphol., Sep. 2005, 13(3):277-82.
Niedringhaus et al., "Landscape of next-generation sequencing technologies," Anal Chem., Jun. 2011, 83(12):4327-41.
Nilsson et al., "RNA-templated DNA ligation for transcript analysis," Nucleic Acids Res., Jan. 2001, 29(2):578-81.
Olivier, "The Invader assay for SNP genotyping," Mutat. Res., Jun. 2005, 573(1-2):103-110.

(56) References Cited

OTHER PUBLICATIONS

Passow et al., "RNAlater and flash freezing storage methods nonrandomly influence observed gene expression in RNAseq experiments," bioRxiv, Jul. 2018, 28 pages.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Piceili et al., "Full-length RNA-seq from single cells using Smart-seq2," Nat Protoc., Jan. 2014, 9(1):171-81.

Porreca et al., "Polony DNA sequencing," Curr Protoc Mol Biol., Nov. 2006, Chapter 7, Unit 7.8, pp. 7.8.1-7.8.22.

Qiu et al., "Combination probes with intercalating anchors and proximal fluorophores for DNA and RNA detection," Nucleic Acids Research, Sep. 2016, 44(17):e138, 12 pages.

Schouten et al., "Relative quantification of 40 nucleic acid sequences by multiplex ligation-dependent probe amplification," Nucleic Acids Res., Jun. 2002, 30(12):e57, 13 pages.

Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.

Singh et al., "High-throughput targeted long-read single cell sequencing reveals the clonal and transcriptional landscape of lymphocytes," Nat Commun., Jul. 2019, 10(1):3120, 13 pages.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Sutherland et al., "Utility of formaldehyde cross-linking and mass spectrometry in the study of protein-protein interactions," J. Mass Spectrom., Jun. 2008, 43(6):699-715.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Tu et al., "TCR sequencing paired with massively parallel 3' RNA-seq reveals clonotypic T cell signatures," Nature Immunology, Dec. 2019, 20(12):1692-1699.

Vázquez Bernat et al., "High-Quality Library Preparation for NGS-Based Immunoglobulin Germline Gene Inference and Repertoire Expression Analysis," Front Immunol., Apr. 2019, 10:660, 12 pages.

Wohnhaas et al., "DMSO cryopreservation is the method of choice to preserve cells for droplet-based single-cell RNA sequencing," Scientific Reports, Jul. 2019, 9(1):10699, 14 pages.

Wu et al., "RollFISH achieves robust quantification of single-molecule RNA biomarkers in paraffin-embedded tumor tissue samples," Commun Biol., Nov. 2018, 1:209, 8 pages.

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Zhao et al., "Isothermal Amplification of Nucleic Acids," Chemical Review's, Nov. 2015. 115(22):12491-12545.

METHODS OF DETERMINING A SURGICAL MARGIN AND METHODS OF USE THEREOF

CROSS REFERENCE TO RELATED APPLICATION

Pursuant to 35 U.S.C. § 119(e), this application is a continuation of International Application PCT/US2021/036415, with an international filing date of Jun. 8, 2021 which claims priority to U.S. Provisional Patent Application No. 63/036,195, filed Jun. 8, 2020. The entire contents of the foregoing application are incorporated herein by reference.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

SUMMARY

Provided herein are method of identifying a surgical margin of a tissue to be resected in a subject, the method comprising: (a) contacting a tissue sample obtained from the subject to an array comprising a plurality of capture probes, wherein a capture probe of the plurality of capture probes comprises (i) a capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin of the tissue to be resected from the subject based on the comparison.

Also provided herein are methods of determining size and site of a tissue to be resected from a subject, the method comprising: (a) contacting a tissue sample obtained from the subject to an array comprising a plurality of capture probes, wherein a capture probe of the plurality of capture probes comprises (i) a capture domain that binds specifically to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at a different location in the tissue sample, and determining the size and site of the tissue to be resected from the subject based on the comparison.

Also provided herein are methods of reducing the risk of re-excision of a tissue, the method comprising: (a) contacting a tissue sample to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin based on the comparison.

Also provided herein are methods of reducing the rate of recurrence of a tissue abnormality in a subject, the method comprising: resecting tissue from the subject using a surgical margin previously determined using a method comprising the steps of: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin based on the comparison.

In some embodiments, the array comprises a slide. In some embodiments, the array is a bead array.

In some embodiments, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing. In some embodiments, step (b) comprises extending a 3' end of the capture probe using the specifically bound analyte as a template to generate an extended capture probe. In some embodiments, step (b) further comprises generating a single-stranded nucleic acid comprising a nucleic acid sequence that is complementary to all or a part of the extended capture probe.

Also provided herein are methods of identifying a surgical margin of a tissue to be resected, the method comprising: (a) contacting a tissue sample to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin of the tissue to be resected based on the comparison.

Also provided herein are methods of determining size and site of a tissue to be resected from a subject, the method comprising: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to the presence of the analyte at different location(s) in the tissue sample, and determining the size and site of the tissue to be resected from the subject based on the comparison.

Also provided herein are methods of reducing the rate of recurrence of a tissue abnormality in a subject, the method comprising: resecting tissue from the subject using a surgical margin previously determined using a method comprising the steps of: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin based on the comparison.

In some embodiments, step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof. In some embodiments, the sequencing is high throughput sequencing. In some embodiments, step (c) comprises extending a 3' end of the capture probe using the specifically bound analyte capture agent as a template to generate an extended capture probe. In some embodiments, step (c) further comprises generating a single-stranded nucleic acid comprising a sequence that is complementary to all or a part of the extended capture probe.

In some embodiments, the array comprises a slide. In some embodiments, the array comprises a slide having the plurality of capture probes. In some embodiments, the array is a bead array.

In some embodiments, the tissue to be resected is a tumor. In some embodiments, the tissue to be resected is infected tissue, necrotic tissue, or diseased tissue. In some embodiments, the resected tissue is a tumor. In some embodiments, the resected tissue is infected tissue, necrotic tissue, or diseased tissue.

In some embodiments, the analyte is RNA. In some embodiments, the RNA is mRNA. In some embodiments, the analyte is DNA. In some embodiments, the DNA is genomic DNA.

In some embodiments, the subject is suspected of or diagnosed as having a cancer. In some embodiments, the cancer is breast cancer. In some embodiments, the subject is suspected of or diagnosed as having ductal carcinoma in situ. In some embodiments, the analyte is a protein. In some embodiments, the protein is an intracellular protein. In some embodiments, the protein is an extracellular protein. In some embodiments, the analyte binding moiety is an antibody or an antigen-binding antibody fragment.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1:
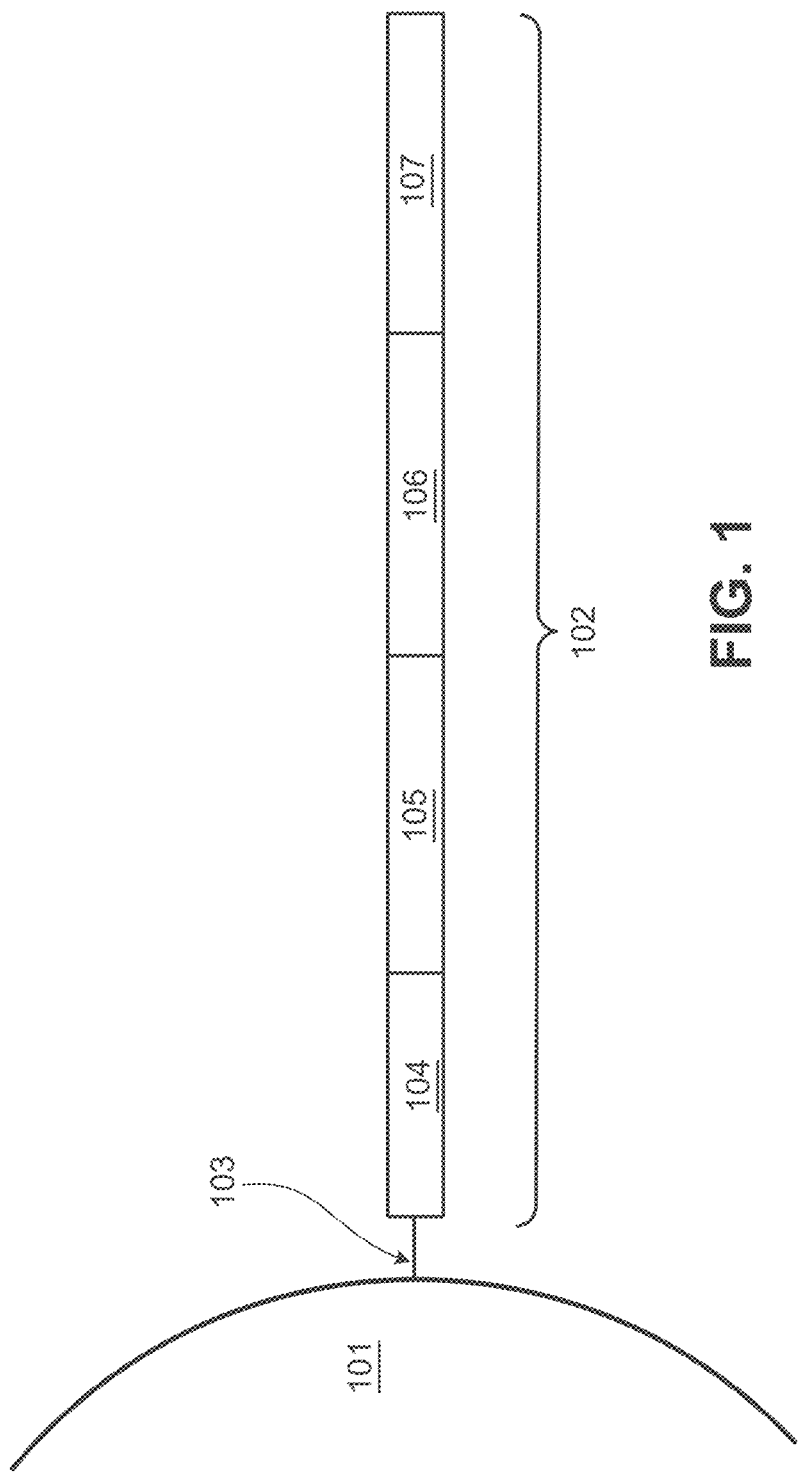
FIG. 1 is a schematic diagram showing an example of a barcoded capture probe, as described herein.

This application is based on the discovery of a method of analyzing spatial expression profiles of analytes in tissue sections and its applications on determining surgical margins and methods of treating patients in need thereof.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that are useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence complementary to a sequence of a nucleic acid analyte, a portion of a connected probe described herein, a capture handle sequence described herein, and/or a methylated adaptor described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature. In some embodiments, the UMI sequence 106 of a capture probe attached to a given feature is different from the UMI sequence of a different capture probe attached to the given feature.

Figure 2:
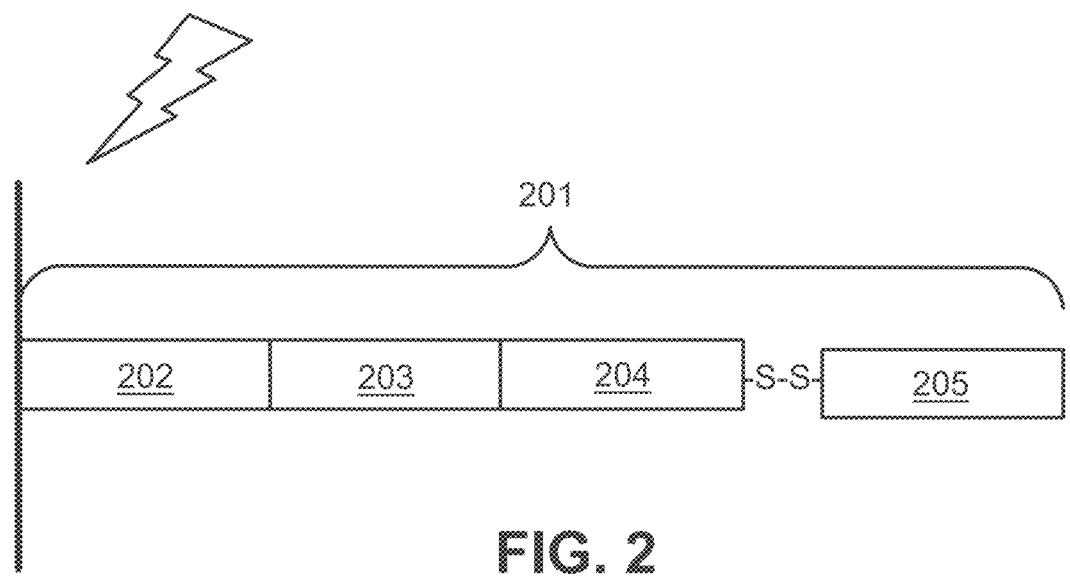
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain. Cleavable capture probe are further described in WO 2020/176788 and/or U.S. Patent Application Publication No. 2020/0277663, each of which is incorporated by reference in its entirety.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 3:
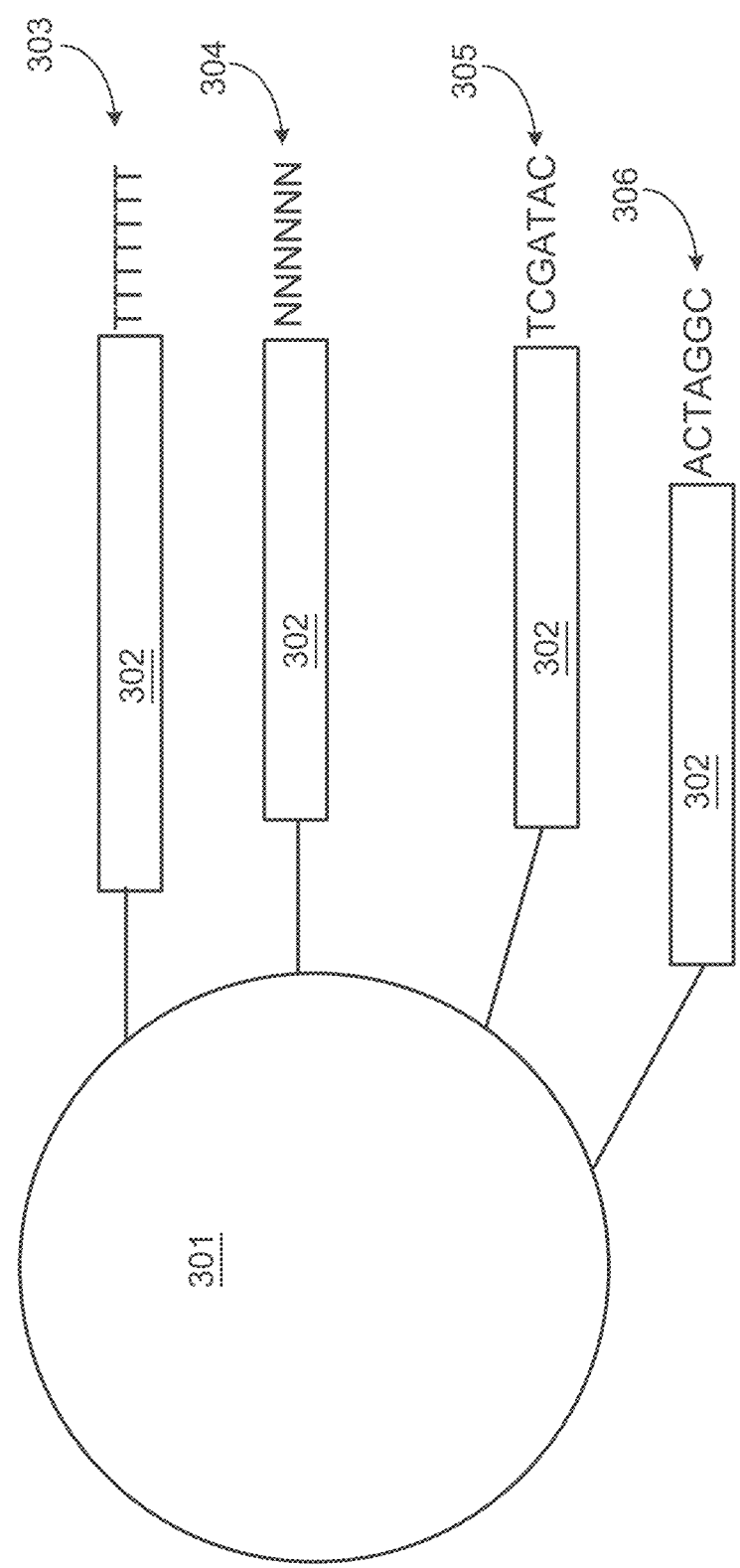
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MEW multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

II. Spatial Analysis

Cancer and disease diagnosis and treatment plans are oftentimes guided by three diagnostic tools: blood work, imaging, and/or biopsies. Oftentimes, surgery is the first line of treatment when cancerous and diseased tissues are identified, especially in the early stages of the disease. When surgery is indicated, clinicians face difficult decisions on the size and site of the resection of the diseased tissue. Conclusive diagnosis and staging are oftentimes obtained after surgical resection has been completed. Unfortunately, sometimes the entire abnormal tissue is not completely removed, leaving tissue margins that contain diseased cells that can proliferate in the body and cause continued cancer and disease.

The methods described here can help support a clinician's decision on the type of surgical intervention to provide a subject with a potential cancer or diseased tissue. For example, information from practicing the described methods can help determine the size and site of tissue resection by more completely identifying abnormal tissue margins, thereby reducing the risk of re-excision and/or reducing the risk of future recurrence of the cancerous or diseased tissue in the subject.

(a) Methods of Determining the Size and Site of a Tissue to be Resected

Provided herein are methods of determining the size and site of a tissue to be resected from a subject that include: (a) contacting a tissue sample obtained from the subject to an array comprising a plurality of capture probes, where a capture probe of the plurality of capture probes comprises (i) a capture domain that binds specifically to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the size and site of a tissue to be resected from the subject based on the comparison. In some embodiments, the analyte is a DNA or RNA. In some embodiments, the analyte is a messenger RNA (mRNA) molecule. In some embodiments, the analyte is a genomic DNA. In some embodiments, the analyte comprises a full-length sequence of a biomarker described herein. In some embodiments, the analyte comprises a fragment of the sequence of a biomarker described herein. In some embodiments of any of the methods described herein, each of the plurality of capture probes comprises (i) a capture domain that binds specifically to an analyte of the tissue section and (ii) a spatial barcode. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the sequence of the analyte of the tissue sample. In some embodiments, the capture domain can have a total of about 10 nucleotides to about 125 nucleotides (or any of the subranges of this range described herein). In some embodiments, the sequence that is substantially complementary to a portion of the sequence of the analyte can be a random sequence. In some embodiments, the sequence that is substantially complementary to a portion of the sequence of the analyte can include a poly(T) oligonucleotide sequence (e.g., at least 5 contiguous Ts, at least 10 contiguous Ts, or at least 15 contiguous Ts).

In some embodiments of any of the methods described herein, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing, sequencing by synthesis, sequencing by hybridization, sequencing by ligation or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to all or a part of the extended capture probe. Non-limiting methods for determining the sequence of (i) all or a part of the sequence of the target nucleic acid, or a complement thereof, or (ii) all or a part of the nucleic acid sequence corresponding to the binding moiety barcode, or a complement thereof, are described herein or are known in the art.

Also provided herein are methods of determining the size and site of a tissue to be resected from a subject that include: (a) contacting a tissue sample obtained from the subject to a plurality of analyte capture agents, where an analyte capture agent of the plurality of analyte capture agents comprises an analyte binding moiety barcode, an analyte capture sequence, and an analyte binding moiety that binds specifically to an analyte; (b) disposing the tissue sample onto an array, where the array comprises a plurality of capture probes, where a capture probe of the plurality of capture probes comprises a spatial barcode and a capture domain that binds specifically to the analyte capture sequence; (c) determining (i) all or a part of the nucleic acid sequence corresponding to the analyte binding moiety barcode or a complement thereof, and (ii) all or a part of the nucleic acid sequence corresponding to the binding moiety barcode or a complement thereof, and using the determined nucleic acid sequences of (i) and (ii) to identify a presence of the analyte at a location in the tissue sample; (d) comparing the presence of the analyte at the location in the tissue sample to presence of the analyte at different location(s) in the tissue sample, and determining the size and site of a tissue to be resected from the subject based on the comparison. In some embodiments, the analyte is a protein. In some embodiments, the analyte is a full-length protein. In some embodiments, the analyte is a fragment of a protein. In some embodiments, the analyte is a byproduct of a protein. In some embodiments, the protein is any of the exemplary cancer biomarkers described herein.

In some embodiments of any of the methods described herein, each of the plurality of analyte capture agents comprises an analyte binding moiety barcode, an analyte capture sequence, and an analyte binding moiety that binds specifically to an analyte. In some embodiments, the analyte binding moiety is an antibody or an antigen-binding antibody fragment (e.g., a Fab). Any other suitable protein binding moiety known in the art can also be used as an analyte binding moiety. In some embodiments, the analyte binding moiety barcode can be any barcode described herein. In some embodiments, the analyte capture sequence can be any analyte capture sequence described herein. In some embodiments of any of the methods described herein, each of the plurality of capture probes comprises a spatial barcode and a capture domain that binds specifically to the analyte capture sequence. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the analyte capture sequence. In some embodiments, the capture domain can have a total of about 10 nucleotides to about 125 nucleotides (or any of the subranges of this range described herein). In some embodiments, the sequence that is substantially complementary to a portion of the analyte capture sequence can be a random sequence. In some embodiments, the sequence that is substantially complementary to a portion of the analyte capture sequence can include a poly(T) oligonucleotide sequence (e.g., at least 5 contiguous Ts, at least 10 contiguous Ts, or at least 15 contiguous Ts).

In some embodiments, the determining of the sequence is by sequencing. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound analyte capture sequence as a template, and generating a single-stranded nucleic acid comprising a sequence that is complementary to all or a part of the extended capture probe. Non-limiting methods for determining the sequence of (i) all or a part of the nucleic acid sequence corresponding to the analyte binding moiety barcode, or a complement thereof, or (ii) all or a part of the nucleic acid sequence corresponding to the spatial barcode, or a complement thereof, are described herein or are known in the art.

In some embodiments, the tissue to be resected is a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein).

Non-limiting examples of cancers referred to in any one the methods described herein include: sarcomas, carcinomas, adrenocortical carcinoma, AIDS-related cancers, anal cancer, appendix cancer, astrocytomas, atypical teratoid/rhabdoid tumor, basal cell carcinoma, bladder cancer, brain stem glioma, brain tumors (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors, and pineoblastoma), breast cancer, bronchial tumors, cancer of unknown primary site, carcinoid tumor, carcinoma of unknown primary site, central nervous system atypical teratoid/rhabdoid tumor, central nervous system embryonal tumors, cervical cancer, childhood cancers, chordoma, colon cancer, colorectal cancer, craniopharyngioma, endocrine pancreas islet cell tumors, endometrial cancer, ependymoblastoma, ependymoma, esophageal cancer, esthesioneuroblastoma, Ewing sarcoma, extracranial germ cell tumor, extragonadal germ cell tumor, extrahepatic bile duct cancer, gallbladder cancer, gastric (stomach) cancer, gastrointestinal carcinoid tumor, gastrointestinal stromal cell tumor, gastrointestinal stromal tumor (GIST), gestational trophoblastic tumor, glioma, head and neck cancer, heart cancer, hypopharyngeal cancer, intraocular melanoma, islet cell tumors, Kaposi's sarcoma, kidney cancer, Langerhans cell histiocytosis, laryngeal cancer, lip cancer, liver cancer, lung cancer, malignant fibrous histiocytoma bone cancer, medulloblastoma, medulloepithelioma, melanoma, Merkel cell carcinoma, Merkel cell skin carcinoma, mesothelioma, metastatic squamous neck cancer with occult primary, mouth cancer, multiple endocrine neoplasia syndromes, multiple myeloma, multiple myeloma/plasma cell neoplasm, mycosis fungoides, myelodysplastic syndromes, myeloproliferative neoplasms, nasal cavity cancer, nasopharyngeal cancer, neuroblastoma, non-melanoma skin cancer, non-small cell lung cancer, oral cancer, oral cavity cancer, oropharyngeal cancer, osteosarcoma, other brain and spinal cord tumors, ovarian cancer, ovarian epithelial cancer, ovarian germ cell tumor, ovarian low malignant potential tumor, pancreatic cancer, papillomatosis, paranasal sinus cancer, parathyroid cancer, pelvic cancer, penile cancer, pharyngeal cancer, pineal parenchymal tumors of intermediate differentiation, pineoblastoma, pituitary tumor, pleuropulmonary blastoma, primary hepatocellular liver cancer, prostate cancer, rectal cancer, renal cancer, renal cell (kidney) cancer, renal cell cancer, respiratory tract cancer, retinoblastoma, rhabdomyosarcoma, salivary gland cancer, Sezary syndrome, small cell lung cancer, small intestine cancer, soft tissue sarcoma, squamous cell carcinoma, squamous neck cancer, stomach (gastric) cancer, supratentorial primitive neuroectodermal tumors, testicular cancer, throat cancer, thymic carcinoma, thymoma, thyroid cancer, transitional cell cancer, transitional cell cancer of the renal pelvis and ureter, trophoblastic tumor, ureter cancer, urethral cancer, uterine cancer, uterine sarcoma, vaginal cancer, vulvar cancer, Waldenström macroglobulinemia, and Wilm's tumor.

In some embodiments, the tissue to be resected can include a tumor (e.g., a malignant tumor) of any of the types of cancer described herein.

In some embodiments of any one of the methods described herein, the analyte is a tumor biomarker. In some embodiments, the analyte is a tumor antigen. Exemplary tumor antigens include, but are not limited to, melanoma-associated antigen (MAGE) series of antigens (e.g., MAGE-C1 (cancer/testis antigen CT7), MAGE-B1 antigen (MAGE-XP antigen, DAM10), MAGE-B2 antigen (DAME), MAGE-2 antigen, MAGE-4a antigen, and MAGE-4b antigen), tyrosinase, glycoprotein 100 (gp100), disialoganglioside GD-2, disialoganglioside 0-acetylated GD-3, ganglioside GM-2, epidermal growth factor receptor (EGFR), vascular endothelial growth factor receptor (VEGFR), mutant B-Raf antigen associated with melanoma and colon cancer, human epidermal growth factor receptor-2 (HER-2/neu) antigen, melanoma-associated antigen recognized by T cells (MART-1) (e.g., MART-1 26-35 peptide or MART-1 27-35 peptide), protein kinase C-binding protein, reverse transcriptase protein, A-kinase-anchoring protein (AKAP protein), vaccinia-related kinase Serine/Threonine Kinase 1(VRK1), fucosyltransferase (T6-7), zinc finger protein 258 (T11-6), p53-binding protein (T1-52), T5-15 (KIAA1735), T5-13 (Sosl), T11-5 (hypothetical protein MGC4170), T11-9 (hypothetical protein AF225417), T11-3 (trap ankyrin repeat), T7-1 (KIAA1288), a mutant or wild type ras peptide, *Homo sapiens* telomerase ferment (hTRT), cytokeratin-19 (CYFRA21-1), squamous cell carcinoma antigen 1 (SCCA-1), protein T4-A, squamous cell carcinoma antigen 2 (SCCA-2), ovarian carcinoma antigen CA125 (1A1-3B) (KIAA0049), cell surface-associated MUCIN 1 (e.g., tumor-associated MUCIN, carcinoma-associated MUCIN, polymorphic epithelial MUCIN peanut-reactive urinary MUCIN, polymorphic epithelial mucin (PEM), PEMT, episialin, tumor-associated epithelial membrane antigen, epithelial membrane antigen (EMA), H23 antigen (H23AG), PUM, and breast carcinoma-associated antigen DF3), CTCL tumor antigen sel-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, prostate-specific membrane antigen, 5T4 oncofetal trophoblast glycoprotein, Orf73 Kaposi's sarcoma-associated herpesvirus, colon cancer antigen NY-CO-45, lung cancer antigen NY-LU-12 variant A, cancer associated surface antigen, adenocarcinoma antigen ART1, paraneoplastic associated brain-testis-cancer antigen (onconeuronal antigen MA2; paraneoplastic neuronal antigen), neuro-oncological ventral antigen 2 (NOVA2), hepatocellular carcinoma antigen gene 520, tumor-associated antigen CO-029, tumor-associated antigen MAGE-X2, synovial sarcoma antigen, X breakpoint 2, squamous cell carcinoma antigen recognized by T cell, serologically defined colon cancer antigen 1, serologically defined breast cancer antigen NY-BR-15, serologically defined breast cancer antigen NY-BR-16, chromogranin A, parathyroid secretory protein 1, pancreatic cancer-associated antigen (DUPAN-2), carbohydrate antigen CA 19-9, carbohydrate antigen CA 72-4, carbohydrate antigen CA 195, and carcinoembryonic antigen (CEA).

In some embodiments, the tissue to be resected is an infected tissue, a necrotic tissue, or a diseased tissue. In some embodiments, the analyte can be associated with an infection, necrosis, inflammation, or disease. Non-limiting examples of such analytes are known in the art.

In some embodiments, the tissue to be resected is infected by a bacterium. In some embodiments, the tissue to be resected is infected by a virus. In some embodiments, the tissue to be resected is infected by a fungus. In some embodiments, the tissue to be resected is infected by a parasite or protozoa.

In some embodiments, the tissue to be resected is infected by a bacterium, e.g., a *Bordetella pertussis*, a *Brucella abortis*, a *Escherichia coli*, a *Salmonella* species, e.g., a *Salmonella typhi*, a *Streptococci*, a *Vibrio* (*V. cholera, V. parahaemolyticus*), a *Shigella*, a *Pseudomonas*, a *Brucella* species, a *Klebsiella*, a *Mycobacteria* species (a tuberculosis, an avium, a BCG, a leprosy), a *Pneumococci*, a *Staphylococci*, a *Enterobacter* species, a *Clostridium tetani*, a *Bacillus anthracis*, a *Streptococcus pneumoniae*, a *Meningococcus* A, B, C, Y, W, or W-135, a *Helicobacter pylori*, a *Rochalimaea henselae*, a *Pasteurella* (*P. haemolytica, P. multocida*), a *Chlamydia* (*C. trachomatis, C. psittaci*), a *Treponema pallidum*, a *Haemophilus* species, e.g., a *Haemophilus* influenza type b, a *mycoplasma* species, a *Borrelia burgdorferi*, a *Legionella pneumophila*, a *Clostridium botu-*

*linum*, a *Corynebacterium diptheriae*, a *Yersinia entercolitica*, a *Ehrlichia*, a *Anaplasma*, or a *Coxiella burnetii* bacterium.

In some embodiments, the tissue to be resected is infected by a parasite or protozoa, e.g., those causing malaria (*Plasmodium falciparum, P. vivax*, or *P. malariae*), a schistosome, a trypanosome, *leishmania*, a filarial nematode, *Trichomonas vaginalis*, a *sarcocystis*, a *Taenia* species (*T. saginata* or *T. solium*), *Toxoplasma gondi, Trichinella spiralis*, or an *Eimeria* species.

In some embodiments, the tissue to be resected is infected by a fungus, e.g., *Cryptococcus neoformans, Candida albicans, Aspergillus fumigatus, Coccidioides immitis*, or *Coccidioides posadasii*.

In some embodiments, the tissue to be resected is infected by a virus, e.g., a rotavirus, an aphthovirus (the agent for foot and mouth disease), an Ebola virus, a Hanta virus, a parainfluenza, a herpes virus species (e.g., herpes simplex virus, Epstein-Barr virus, chicken pox virus, pseudorabies, or cytomegalovirus), a rabies virus, a polio virus, a Hepatitis A, B, C or E, distemper, a Venezuelan equine encephalomyelitis virus, a feline leukemia virus, a reovirus, a respiratory syncytial virus, a Lassa fever virus, a polyoma virus, a canine parvovirus, a papilloma virus, a flavivirus, a tick borne encephalitis virus, a paramyxovirus (the agent for Rinderpest), a rhinovirus, an enterovirus, a Mengo virus, a paramyxovirus (mumps, measles, or respiratory syncytial virus), an avian infectious bronchitis virus, HTLV 1, HIV-1 or -2, or influenza virus A, B, or C, a lymphocytic choriomeningitis virus, a parvovirus, an adenovirus, a togavirus, a bovine respiratory syncytial virus, a coronavirus, or a Japanese Encephalitis virus.

In some embodiments, the methods provided herein comprise comparing the presence of the analyte at the location in the tissue sample to presence of the analyte at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the analyte at the location in the tissue sample is significantly different from the presence of the analyte at the different location(s) in the tissue. In some embodiments, the presence of the analyte at the location in the tissue sample is significantly greater than the presence of the analyte at the different location(s) in the tissue sample. In some embodiments, the presence of the analyte at the location in the tissue sample is significantly less than the presence of the analyte at the different location(s) in the tissue sample.

In some embodiments, the location at the tissue sample is determined to be resected if the presence of the analyte at the location in the tissue sample is significantly different from the presence of the analyte at the different location(s). In some embodiments, the location at the tissue sample is determined to be resected if the presence of the analyte at the location in the tissue sample is significantly greater than the presence of the analyte at the different location(s). In some embodiments, the location at the tissue sample is determined to be resected if the presence of the analyte at the location in the tissue sample is significantly less than the presence of the analyte at the different location(s).

In some embodiments, the presence of the analyte at the location in the tissue sample is about 0.1-fold to about 100-fold (e.g., about 0.1-fold to about 90-fold, about 0.1-fold to about 80-fold, about 0.1-fold to about 70-fold, about 0.1-fold to about 60-fold, about 0.1-fold to about 50-fold, about 0.1-fold to about 40-fold, about 0.1-fold to about 30-fold, about 0.1-fold to about 20-fold, about 0.1-fold to about 15-fold, about 0.1-fold to about 10-fold, about 0.1-fold to about 8-fold, about 0.1-fold to about 6-fold, about 0.1-fold to about 5-fold, about 0.1-fold to about 4-fold, about 0.1-fold to about 3-fold, about 0.1-fold to about 2-fold, about 0.1-fold to about 1.5-fold, about 0.1-fold to about 1-fold, about 0.1-fold to about 0.8-fold, about 0.1-fold to about 0.6-fold, about 0.1-fold to about 0.4-fold, about 0.1-fold to about 0.2-fold, about 1-fold to about 100-fold, about 1-fold to about 90-fold, about 1-fold to about 80-fold, about 1-fold to about 70-fold, about 1-fold to about 60-fold, about 1-fold to about 50-fold, about 1-fold to about 40-fold, about 1-fold to about 30-fold, about 1-fold to about 20-fold, about 1-fold to about 15-fold, about 1-fold to about 10-fold, about 1-fold to about 8-fold, about 1-fold to about 6-fold, about 1-fold to about 5-fold, about 1-fold to about 4-fold, about 1-fold to about 3-fold, about 1-fold to about 2-fold, about 1-fold to about 1.5-fold, about 5-fold to about 100-fold, about 5-fold to about 90-fold, about 5-fold to about 80-fold, about 5-fold to about 70-fold, about 5-fold to about 60-fold, about 5-fold to about 50-fold, about 5-fold to about 40-fold, about 5-fold to about 30-fold, about 5-fold to about 20-fold, about 5-fold to about 15-fold, about 5-fold to about 10-fold, about 5-fold to about 8-fold, about 5-fold to about 6-fold, about 10-fold to about 100-fold, about 10-fold to about 90-fold, about 10-fold to about 80-fold, about 10-fold to about 70-fold, about 10-fold to about 60-fold, about 10-fold to about 50-fold, about 10-fold to about 40-fold, about 10-fold to about 30-fold, about 10-fold to about 20-fold, about 10-fold to about 15-fold, about 15-fold to about 100-fold, about 15-fold to about 90-fold, about 15-fold to about 80-fold, about 15-fold to about 70-fold, about 15-fold to about 60-fold, about 15-fold to about 50-fold, about 15-fold to about 40-fold, about 15-fold to about 30-fold, about 15-fold to about 20-fold, about 20-fold to about 100-fold, about 20-fold to about 90-fold, about 20-fold to about 80-fold, about 20-fold to about 70-fold, about 20-fold to about 60-fold, about 20-fold to about 50-fold, about 20-fold to about 40-fold, about 20-fold to about 30-fold, about 30-fold to about 40-fold, about 40-fold to about 100-fold, about 40-fold to about 90-fold, about 40-fold to about 80-fold, about 40-fold to about 70-fold, about 40-fold to about 60-fold, about 40-fold to about 50-fold, about 50-fold to about 100-fold, about 50-fold to about 90-fold, about 50-fold to about 80-fold, about 50-fold to about 70-fold, about 50-fold to about 60-fold, about 60-fold to about 100-fold, about 60-fold to about 90-fold, about 60-fold to about 80-fold, about 60-fold to about 70-fold, about 70-fold to about 100-fold, about 70-fold to about 90-fold, about 70-fold to about 80-fold, about 80-fold to about 100-fold, about 80-fold to about 90-fold, or about 90-fold to about 100-fold) greater than the presence of the analyte at the different location(s).

In some embodiments, the presence of the analyte at the location in the tissue sample is about 1% to about 99% (e.g., about 1% to about 95%, about 1% to about 90%, about 1% to about 85%, about 1% to about 80%, about 1% to about 75%, about 1% to about 70%, about 1% to about 65%, about 1% to about 60%, about 1% to about 55%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 99%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 99%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 10% to about 15%, about 20% to about 99%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 20% to about 25%, about 30% to about 99%, about 30% to about 95%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, about 30% to about 40%, about 30% to about 35%, about 40% to about 99%, about 40% to about 95%, about 40% to about 90%, about 40% to about 85%, about 40% to about 80%, about 40% to about 75%, about 40% to about 70%, about 40% to about 65%, about 40% to about 60%, about 40% to about 55%, about 40% to about 50%, about 40% to about 45%, about 50% to about 99%, about 50% to about 95%, about 50% to about 90%, about 50% to about 85%, about 50% to about 80%, about 50% to about 75%, about 50% to about 70%, about 50% to about 65%, about 50% to about 60%, about 50% to about 55%, about 60% to about 99%, about 60% to about 95%, about 60% to about 90%, about 60% to about 85%, about 60% to about 80%, about 60% to about 75%, about 60% to about 70%, about 60% to about 65%, about 70% to about 99%, about 70% to about 95%, about 70% to about 90%, about 70% to about 85%, about 70% to about 80%, about 70% to about 75%, about 80% to about 99%, about 80% to about 95%, about 80% to about 90%, about 80% to about 85%, about 90% to about 99%, about 90% to about 95%, or about 95% to about 99%) decreased than the presence of the analyte at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of tissue to be resected.

In some embodiments, the method further comprises comparing presence of one or more additional analyte(s) at the location in the tissue sample with the presence of the one or more additional analyte(s) at the different location(s) in the tissue sample. In some embodiments, the presence of a total of about 1 to about 20,000 (e.g., about 1 to about 18,000, about 1 to about 16,000, about 1 to about 14,000, about 1 to about 12,000, about 1 to about 10,000, about 1 to about 9,000, about 1 to about 8,000, about 1 to about 7,000, about 1 to about 6,000, about 1 to about 5,000, about 1 to about 4,500, about 1 to about 4,000, about 1 to about 3,500, about 1 to about 3,000, about 1 to about 2,500, about 1 to about 2,000, about 1 to about 1,500, about 1 to about 1,000, about 1 to about 800, about 1 to about 600, about 1 to about 500, about 1 to about 400, about 1 to about 300, about 1 to about 200, about 1 to about 100, about 1 to about 50, about 1 to about 20, about 1 to about 10, about 1 to about 5, about 50 to about 20,000, about 50 to about 18,000, about 50 to about 16,000, about 50 to about 14,000, about 50 to about 12,000, about 50 to about 10,000, about 50 to about 9,000, about 50 to about 8,000, about 50 to about 7,000, about 50 to about 6,000, about 50 to about 5,000, about 50 to about 4,500, about 50 to about 4,000, about 50 to about 3,500, about 50 to about 3,000, about 50 to about 2,500, about 50 to about 2,000, about 50 to about 1,500, about 50 to about 1,000, about 50 to about 800, about 50 to about 600, about 50 to about 500, about 50 to about 400, about 50 to about 300, about 50 to about 200, about 50 to about 100, about 100 to about 20,000, about 100 to about 18,000, about 100 to about 16,000, about 100 to about 14,000, about 100 to about 12,000, about 100 to about 10,000, about 100 to about 9,000, about 100 to about 8,000, about 100 to about 7,000, about 100 to about 6,000, about 100 to about 5,000, about 100 to about 4,500, about 100 to about 4,000, about 100 to about 3,500, about 100 to about 3,000, about 100 to about 2,500, about 100 to about 2,000, about 100 to about 1,500, about 100 to about 1,000, about 100 to about 800, about 100 to about 600, about 100 to about 500, about 100 to about 400, about 100 to about 300, about 100 to about 200, about 500 to about 20,000, about 500 to about 18,000, about 500 to about 16,000, about 500 to about 14,000, about 500 to about 12,000, about 500 to about 10,000, about 500 to about 9,000, about 500 to about 8,000, about 500 to about 7,000, about 500 to about 6,000, about 500 to about 5,000, about 500 to about 4,500, about 500 to about 4,000, about 500 to about 3,500, about 500 to about 3,000, about 500 to about 2,500, about 500 to about 2,000, about 500 to about 1,500, about 500 to about 1,000, about 500 to about 800, about 500 to about 600, about 1,000 to about 20,000, about 1,000 to about 18,000, about 1,000 to about 16,000, about 1,000 to about 14,000, about 1,000 to about 12,000, about 1,000 to about 10,000, about 1,000 to about 9,000, about 1,000 to about 8,000, about 1,000 to about 7,000, about 1,000 to about 6,000, about 1,000 to about 5,000, about 1,000 to about 4,500, about 1,000 to about 4,000, about 1,000 to about 3,500, about 1,000 to about 3,000, about 1,000 to about 2,500, about 1,000 to about 2,000, about 1,000 to about 1,500, about 1,500 to about 20,000, about 2,000 to about 20,000, about 2,000 to about 18,000, about 2,000 to about 16,000, about 2,000 to about 14,000, about 2,000 to about 12,000, about 2,000 to about 10,000, about 2,000 to about 9,000, about 2,000 to about 8,000, about 2,000 to about 7,000, about 2,000 to about 6,000, about 2,000 to about 5,000, about 2,000 to about 4,500, about 2,000 to about 4,000, about 2,000 to about 3,500, about 2,000 to about 3,000, about 2,000 to about 2,500, about 5,000 to about 20,000, about 5,000 to about 18,000, about 5,000 to about 16,000, about 5,000 to about 14,000, about 5,000 to about 12,000, about 5,000 to about 10,000, about 5,000 to about 9,000, about 5,000 to about 8,000, about 5,000 to about 7,000, about 5,000 to about 6,000, about 10,000 to about 20,000, about 10,000 to about 18,000, about 10,000 to about 16,000, about 10,000 to about 14,000, about 10,000 to about 12,000, about 12,000 to about 20,000, about 12,000 to about 18,000, about 12,000 to about 16,000, about 12,000 to about 14,000, about 14,000 to about 20,000, about 14,000 to about 18,000, about 14,000 to about 16,000, about 16,000 to about 20,000, about 16,000 to about 18,000, or about 18,000 to about 20,000) analyte(s) at the location are compared to the presence of the analyte(s) at the different location(s).

In some embodiments of any one of the methods described herein, mutant cells are identified according to the presence of the one or more analyte(s) at the location in the tissue sample. In some embodiments, a mutant cell is identified according to the presence of one or more biomarkers described herein. In some embodiments, a mutant cell is identified according to the presence of one or more cell-surface biomarkers, e.g., a cell-surface receptor, at the location in the tissue sample.

In some embodiments, a cell within a location at the tissue sample is identified as a mutant cell if the presence of the one or more analyte(s) at the location in the tissue sample are significantly different from the presence of the analyte(s) at the different location(s). In some embodiments, a cell within a location at the tissue sample is identified as a mutant cell if the presence of the one or more analyte(s) at the location in the tissue sample are significantly greater than the presence of the analyte(s) at the different location(s). In some embodiments, the mutant cell(s) within the location at the tissue sample is determined to be resected if the presence of the analyte(s) at the location in the tissue sample are significantly less than the presence of the analyte at the different location(s).

In some embodiments, a location at the tissue sample comprises about 1 to about 100,000 (e.g., about 1 to about 90,000, about 1 to about 80,000, about 1 to about 70,000, about 1 to about 60,000, about 1 to about 50,000, about 1 to about 40,000, about 1 to about 30,000, about 1 to about 20,000, about 1 to about 10,000, about 1 to about 9,000, about 1 to about 8,000, about 1 to about 7,000, about 1 to about 6,000, about 1 to about 5,000, about 1 to about 4,000, about 1 to about 3,000, about 1 to about 2,000, about 1 to about 1,000, about 1 to about 900, about 1 to about 800, about 1 to about 700, about 1 to about 600, about 1 to about 500, about 1 to about 400, about 1 to about 300, about 1 to about 200, about 1 to about 100, about 1 to about 90, about 1 to about 80, about 1 to about 70, about 1 to about 60, about 1 to about 50, about 1 to about 40, about 1 to about 30, about 1 to about 20, about 1 to about 10, about 100 to about 100,000, about 100 to about 90,000, about 100 to about 80,000, about 100 to about 70,000, about 100 to about 60,000, about 100 to about 50,000, about 100 to about 40,000, about 100 to about 30,000, about 100 to about 20,000, about 100 to about 10,000, about 100 to about 9,000, about 100 to about 8,000, about 100 to about 7,000, about 100 to about 6,000, about 100 to about 5,000, about 100 to about 4,000, about 100 to about 3,000, about 100 to about 2,000, about 100 to about 1,000, about 100 to about 900, about 100 to about 800, about 100 to about 700, about 100 to about 600, about 100 to about 500, about 100 to about 400, about 100 to about 300, about 100 to about 200, about 1,000 to about 100,000, about 1,000 to about 90,000, about 1,000 to about 80,000, about 1,000 to about 70,000, about 1,000 to about 60,000, about 1,000 to about 50,000, about 1000 to about 40,000, about 1,000 to about 30,000, about 1,000 to about 20,000, about 1,000 to about 10,000, about 1000 to about 9,000, about 1,000 to about 8,000, about 1,000 to about 7,000, about 1000 to about 6,000, about 1,000 to about 5,000, about 1,000 to about 4,000, about 1000 to about 3,000, about 1,000 to about 2,000, 10,000 to about 100,000, about 10,000 to about 90,000, about 10,000 to about 80,000, about 10,000 to about 70,000, about 10,000 to about 60,000, about 10000 to about 50,000, about 10,000 to about 40,000, about 10,000 to about 30,000, about 10,000 to about 20,000) cells.

In some embodiments of any one of the methods described herein, the tissue sample can be obtained from any suitable tissue or organ from the subject (e.g., breast tissue, muscle tissue, gland tissue, fat or adipose tissue, nerve tissue, joint tissue, ligament tissue, tendon tissue, mouth tissue, tongue tissue, salivary gland tissue, parotid gland tissue, submandibular gland tissue, sublingual gland tissue, pharynx tissue, esophageal tissue, stomach tissue, small intestine tissue, duodenum tissue, jejunum tissue, ileum tissue, large intestine tissue, liver tissue, gallbladder tissue, mesentery tissue, pancreas tissue, anal canal tissue, anus tissue, nasal cavity tissue, pharynx tissue, larynx tissue, trachea tissue, bronchi tissue, lung tissue, diaphragm tissue, kidney tissue, ureter tissue, bladder tissue, urethra tissue, ovarian tissue, fallopian tube tissue, uterus tissue, vagina tissue, vulva tissue, clitoris tissue, testes tissue, epididymis tissue, vas deferens tissue, seminal vesicles tissue, prostate tissue, bulbourethral gland tissue, external reproductive organ tissue, penis tissue, scrotum tissue, brain tissue, pituitary gland tissue, pineal gland tissue, thyroid gland tissue, parathyroid gland tissue, adrenal gland tissue, pancreas tissue, heart tissue, patent foramen ovale tissue, artery tissue, vein tissue, capillary tissue, lymphatic vessel tissue, lymph node tissue, bone tissue, thymus tissue, spleen tissue, gut-associated lymphoid tissue, tonsil tissue, interstitium tissue, cerebrum tissue, cerebral hemisphere tissue, diencephalon tissue, brainstem tissue, midbrain tissue, pons tissue, medulla oblongata tissue, cerebellum tissue, spinal cord tissue, ventricular system tissue, choroid plexus tissue, nerve tissue, cranial nerve tissue, spinal nerve tissue, Anglia tissue, enteric nervous system tissue, eye tissue, a cornea tissue, iris tissue, ciliary body tissue, lens tissue, retina tissue, ear tissue, outer ear tissue, earlobe tissue, eardrum tissue, middle ear tissue, ossicles tissue, inner ear tissue, cochlea tissue, vestibule tissue, semicircular canal tissue, olfactory epithelium tissue, tongue tissue, taste bud tissue, mammary gland tissue, skin tissue, subcutaneous tissue, and milk duct tissue). In some embodiments, the tissue sample can include or be proximal in the body of the subject to a nerve, a blood vessel, and/or a lymph vessel.

The spatial barcode of the capture probe can be any spatial barcode described herein.

In some embodiments of any of the methods described herein, the array can be any of the types of arrays described herein. For example, the array comprises a slide. In some embodiments, the capture probe is attached to the slide (e.g., by its 5' end).

In some embodiments of any of the methods described herein, the array is a bead array. In some embodiments, a 5' end of the capture probe is attached to a bead of the bead array.

In some embodiments of any of the methods described herein, the method comprises extending a 3' end of the capture probe using the specifically bound analyte or analyte binding agent barcode as a template to generate an extended capture probe.

In some embodiments, additional methods are used in combination with the methods described herein to determine the site and size of the tissue to be resected in a subject. In some embodiments, medical imaging modalities such as computed tomography (CT) and magnetic resonance imaging (MRI) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., MRI, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy from the subject).

In some embodiments of any of the methods described herein, at least a portion of the tissue to be resected includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the tissue to be resected includes one or more of cancer cell(s), pre-cancerous cell(s), necrotic cell(s), infected cell(s), and disease tissue.

(b) Methods of Treating a Subject by Resecting Tissue

Also provided herein are methods of treating a subject in need thereof that include: (a) contacting a tissue sample obtained from the subject to an array comprising a plurality of capture probes, wherein a capture probe of the plurality of capture probes comprises (i) a capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at a different location in the tissue sample, and determining the surgical margin based on the comparison; and (d) resecting tissue from the subject using the surgical margin determined in step (c).

A method of treating a subject, the method comprising: resecting tissue from the subject using a surgical margin previously determined using a method comprising the steps of: (a) contacting a tissue sample obtained from the subject to an array comprising a plurality of capture probes, wherein a capture probe of the plurality of capture probes comprises (i) a capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to the presence of the analyte at a different location in the tissue sample, and determining the surgical margin based on the comparison.

For example, when a clinician practices the method, the data obtained can provide the clinician with information on the accurate location of the cancerous or diseased tissue, therefore provide the accurate surgical margin of the tissue to be resected. Using the information of the accurate surgical margin provided by the method described herein, the clinician is able to achieve, e.g., more complete resection, thereby treating the subject.

In some embodiments, the analyte is a DNA or RNA. In some embodiments, the analyte is a messenger RNA (mRNA) molecule. In some embodiments, the analyte is a genomic DNA. In some embodiments, the analyte comprises a full-length sequence of a biomarker described herein. In some embodiments, the analyte comprises a fragment of the sequence of a biomarker described herein. In some embodiments of any of the methods described herein, each of the plurality of capture probes comprises (i) a capture domain that binds specifically to an analyte of the tissue sample and (ii) a spatial barcode. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the sequence of the analyte of the tissue sample. In some embodiments, the capture domain can have a total of about 10 nucleotides to about 125 nucleotides (or any of the subranges of this range described herein). In some embodiments, the sequence that is substantially complementary to a portion of the sequence of the analyte can be a random sequence. In some embodiments, the sequence that is substantially complementary to a portion of the sequence of the analyte can include a poly(T) oligonucleotide sequence (e.g., at least 5 contiguous Ts, at least 10 contiguous Ts, or at least 15 contiguous Ts).

In some embodiments of any of the methods described herein, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to all or a part of the extended capture probe. Non-limiting methods for determining the sequence of (i) all or a part of the sequence of the target nucleic acid, or a complement thereof, or (ii) all or a part of the nucleic acid sequence corresponding to the spatial barcode, or a complement thereof, are described herein or are known in the art.

Also provided herein are methods of treating a subject that include: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin based on the comparison; and (e) resecting tissue from the subject using the surgical margin determined in step (d).

Also provided herein are methods of treating a subject, the method comprising: resecting tissue from the subject using a surgical margin previously determined using a method comprising the steps of: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin based on the comparison.

In some embodiments, the analyte is a protein. In some embodiments, the analyte is a full-length protein. In some embodiments, the analyte is a fragment of a protein. In some embodiments, the analyte is a byproduct of a protein. In some embodiments, the protein is any of the exemplary cancer biomarkers described herein.

In some embodiments of any of the methods described herein, each of the plurality of analyte capture agents comprises an analyte binding moiety barcode, an analyte capture sequence, and an analyte binding moiety that binds specifically to an analyte. In some embodiments, the analyte binding moiety is an antibody or an antigen-binding antibody fragment (e.g., a Fab). Any other suitable protein binding moiety known in the art can also be used as an analyte binding moiety. In some embodiments, the analyte binding moiety barcode can be any barcode described herein. In some embodiments, the analyte capture sequence can be any analyte capture sequence described herein. In some embodiments of any of the methods described herein, each of the plurality of capture probes comprises a spatial barcode and a capture domain that binds specifically to the analyte capture sequence.

The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the analyte capture sequence. In some embodiments, the capture domain can have a total of about 10 nucleotides to about 125 nucleotides (or any of the subranges of this range described herein). In some embodiments, the sequence that is substantially complementary to a portion of the analyte capture sequence can be a random sequence. In some embodiments, the sequence that is substantially complementary to a portion of the analyte capture sequence can include a poly(T) oligonucleotide sequence (e.g., at least 5 contiguous Ts, at least 10 contiguous Ts, or at least 15 contiguous Ts).

In some embodiments, the determining of the sequence is by sequencing. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound analyte capture sequence as a template, and generating a single-stranded nucleic acid comprising a sequence that is complementary to all or a part of the extended capture probe. Non-limiting methods for determining the sequence of (i) all or a part of the nucleic acid sequence corresponding to the analyte binding moiety barcode, or a complement thereof, or (ii) all or a part of the nucleic acid sequence corresponding to the spatial barcode, or a complement thereof, are described herein or are known in the art.

In some embodiments, the resected tissue is or comprises a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein).

In some embodiments, the resected tissue can include a tumor, (e.g., a malignant tumor) of any of the types of cancer describes herein.

In some embodiments, the analyte is a tumor biomarker. In some embodiments, the analyte is a tumor antigen. Exemplary tumor antigens include, but are not limited to, any of the exemplary tumor antigens described herein.

In some embodiments, the resected tissue is or comprises an infected tissue, a necrotic tissue, or a diseased tissue. In some embodiments, the analyte can be associated with an infection, necrosis, inflammation, or disease. Non-limiting examples of such analytes are known in the art.

In some embodiments, the resected tissue is infected by a bacterium (e.g., any of the exemplary bacteria described herein), a parasite or protozoa (e.g., any of the exemplary parasites or protozoa described herein), a fungus (e.g., any of the exemplary fungi described herein), or a virus (e.g., any of the exemplary viruses described herein).

In some embodiments, the methods provided herein comprise comparing the presence of the analyte at the location in the tissue sample to the presence of the analyte at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the analyte at the location in the tissue sample is significantly different from the presence of the analyte at the different location(s) in the tissue. In some embodiments, the presence of the analyte at the location in the tissue sample is significantly greater than the presence of the analyte at the different location(s) in the tissue sample. In some embodiments, the presence of the analyte at the location in the tissue sample is significantly less than the presence of the analyte at the different location(s) in the tissue sample.

In some embodiments, the location at the tissue sample is determined to be resected if the presence of the analyte at the location in the tissue sample is significantly different from the presence of the analyte at the different location(s). In some embodiments, the location at the tissue sample is determined to be resected if the presence of the analyte at the location in the tissue sample is significantly greater than the presence of the analyte at the different location(s). In some embodiments, the location at the tissue sample is determined to be resected if the presence of the analyte at the location in the tissue sample is significantly less than the presence of the analyte at the different location(s).

In some embodiments, the presence of the analyte at the location in the tissue sample is about 0.1-fold to about 100-fold (e.g., or any of the subranges of this range described herein) greater than the presence of the analyte at the different location(s).

In some embodiments, the presence of the analyte at the location in the tissue sample is about 1% to about 99% (e.g., or any of the subranges of this range described herein) decreased than the presence of the analyte at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of tissue to be resected.

In some embodiments, the method further comprises comparing the presence of one or more additional analyte(s) at the location in the tissue sample with the presence of the one or more additional analyte(s) at the different location(s) in the tissue sample. In some embodiments, the presence of a total of about 1 to about 20,000 (e.g., or any of the subranges of this range described herein) analyte(s) at the location are compared to the presence of the analyte(s) at the different location(s).

In some embodiments of any one of the methods described herein, mutant cells are identified according to the presence of the one or more analyte(s) at the location in the tissue sample. In some embodiments, a mutant cell is identified according to the presence of one or more biomarkers described herein. In some embodiments, a mutant cell is identified according to the presence of one or more cell-surface biomarkers, e.g., a cell-surface receptor, at the location in the tissue sample.

In some embodiments, a cell within a location at the tissue sample is identified as a mutant cell if the presence of the one or more analyte(s) at the location in the tissue sample are significantly different from the presence of the analyte(s) at the different location(s). In some embodiments, a cell within a location at the tissue sample is identified as a mutant cell if the presence of the one or more analyte(s) at the location in the tissue sample are significantly greater than the presence of the analyte(s) at the different location(s). In some embodiments, the mutant cell(s) within the location at the tissue sample is determined to be resected if the presence of the analyte(s) at the location in the tissue sample are significantly less than the presence of the analyte at the different location(s).

In some embodiments, a location at the tissue sample comprises about 1 to about 100,000 cells.

The spatial barcode of the capture probe can be any spatial barcode described herein.

In some embodiments of any of the methods described herein, the array can be any of the types of arrays described herein. For example, the array comprises a slide. In some embodiments, the capture probe is attached to the slide (e.g., by its 5' end).

In some embodiments of any of the methods described herein, the array is a bead array. In some embodiments, a 5' end of the capture probe is attached to a bead of the bead array.

In some embodiments of any of the methods described herein, the method comprises extending a 3' end of the capture probe using the specifically bound analyte or analyte binding agent barcode as a template to generate an extended capture probe.

In some embodiments, additional methods are used in combination with the methods described herein to determine the site and size of the tissue to be resected in a subject. In some embodiments, medical imaging modalities such as computed tomography (CT) and magnetic resonance imaging (MRI) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., MRI, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy sample from the subject).

In some embodiments of any of the methods described herein, at least a portion of the resected tissue includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the resected tissue includes one or more of cancer cell(s), pre-cancerous cell(s), necrotic cell(s), infected cell(s), and disease tissue.

In some embodiments, the tissue resection is considered successful when less than 20%, less than 15%, less than 10%, less than 5%, or zero cancer cell(s), pre-cancerous cell(s), necrotic cell(s), infected cell(s), and/or diseased tissue are detected post-resection as compared to the identified cancer cell(s), pre-cancerous cell(s), necrotic cell(s), infected cell(s), and/or diseased tissue prior to the resection.

In some embodiments, the treatment is considered successful when less than 20%, less than 15%, less than 10%, less than 5%, or zero cancer cell(s), pre-cancerous cell(s), necrotic cell(s), infected cell(s), and/or diseased tissue are detected post-resection as compared to the identified cancer cell(s), pre-cancerous cell(s), necrotic cell(s), infected cell(s), and/or diseased tissue prior to the resection.

In some embodiments of any of the methods described herein, the surgical margin can be the margin between the location(s) of one or more of cancer cell(s), pre-cancerous cell(s), necrotic cell(s), infected cell(s), and disease tissue, and the location(s) of healthy or normal tissue, in a subject.

(c) Methods of Identifying a Surgical Margin of a Tissue to be Resected

Provided herein are methods of identifying a surgical margin of a tissue to be resected in a subject, the method comprising: (a) contacting a tissue sample obtained from the subject to an array comprising a plurality of capture probes, wherein a capture probe of the plurality of capture probes comprises (i) a capture domain that specifically binds to an analyte of the tissue sample and (ii) a spatial barcode; (b) determining (i) all or a part of the nucleic acid sequence corresponding to the analyte specifically bound to the capture domain or a complement thereof, and (ii) all or a part of the nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to the presence of the analyte at different location(s) in the tissue sample, and determining a surgical margin of a tissue to be resected from the subject based on the comparison. In some embodiments, the analyte is a DNA or RNA. In some embodiments, the analyte is a messenger RNA (mRNA) molecule. In some embodiments, the analyte is a genomic DNA. In some embodiments, the analyte comprises a full-length sequence of a biomarker described herein. In some embodiments, the analyte comprises a fragment of the sequence of a biomarker described herein. In some embodiments of any of the methods described herein, each of the plurality of capture probes comprises (i) a capture domain that binds specifically to an analyte of the tissue sample and (ii) a spatial barcode. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the sequence of the analyte of the tissue sample. In some embodiments, the capture domain can have a total of about 10 nucleotides to about 125 nucleotides (or any of the subranges of this range described herein). In some embodiments, the sequence that is substantially complementary to a portion of the sequence of the analyte can be a random sequence. In some embodiments, the sequence that is substantially complementary to a portion of the sequence of the analyte can include a poly(T) oligonucleotide sequence (e.g., at least 5 contiguous Ts, at least 10 contiguous Ts, or at least 15 contiguous Ts).

In some embodiments of any of the methods described herein, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to all or a part of the extended capture probe. Non-limiting methods for determining the sequence of (i) all or a part of the sequence of the target nucleic acid, or a complement thereof, or (ii) all or a part of the nucleic acid sequence corresponding to the spatial barcode, or a complement thereof, are described herein or are known in the art.

Provided herein are methods of identifying a surgical margin of a tissue to be resected in a subject that include: (a) contacting a tissue sample obtained from the subject to a plurality of analyte capture agents, where an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, where a capture probe of the plurality of capture probes comprises a spatial barcode and a capture domain that binds specifically to the analyte capture sequence; (c) determining (i) all or a part of the nucleic acid sequence corresponding to the analyte binding moiety barcode or a complement thereof, and (ii) all or a part of the nucleic acid sequence corresponding to the spatial barcode or a complement thereof, and using the determined nucleic acid sequences of (i) and (ii) to identify the presence of the analyte at a location in the tissue sample; (d) comparing the the presence of the analyte at the location in the tissue sample to presence of the analyte at different location(s) in the tissue sample, and determining a surgical margin of a tissue to be resected from the subject based on the comparison. In some embodiments, the analyte is a protein. In some embodiments, the analyte is a full-length protein. In some embodiments, the analyte is a fragment of a protein. In some embodiments, the analyte is a byproduct of a protein. In some embodiments, the protein is any of the exemplary cancer biomarkers described herein.

In some embodiments of any of the methods described herein, each of the plurality of analyte capture agents comprises an analyte binding moiety barcode, an analyte capture sequence, and an analyte binding moiety that binds specifically to an analyte. In some embodiments, the analyte binding moiety is an antibody or an antigen-binding antibody fragment (e.g., a Fab). Any other suitable protein binding moiety known in the art can also be used as an analyte binding moiety. In some embodiments, the analyte binding moiety barcode can be any barcode described herein. In some embodiments, the analyte capture sequence can be any analyte capture sequence described herein. In some embodiments of any of the methods described herein, each of the plurality of capture probes comprises a spatial barcode and a capture domain that binds specifically to the analyte capture sequence. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the analyte capture sequence. In some embodiments, the capture domain can have a total of about 10 nucleotides to about 125 nucleotides (or any of the subranges of this range described herein). In some embodiments, the sequence that is substantially complementary to a portion of the analyte capture sequence can be a random sequence. In some embodiments, the sequence that is substantially complementary to a portion of the analyte capture sequence can include a poly(T) oligonucleotide sequence (e.g., at least 5 contiguous Ts, at least 10 contiguous Ts, or at least 15 contiguous Ts).

In some embodiments, the determining of the sequence is by sequencing. In some embodiments, the sequencing is high throughput sequencing, sequencing by hybridization, sequencing by ligation or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound analyte capture sequence as a template, and generating a single-stranded nucleic acid comprising a sequence that is complementary to all or a part of the extended capture probe. Non-limiting methods for determining the sequence of (i) all or a part of the nucleic acid sequence corresponding to the analyte binding moiety barcode, or a complement thereof, or (ii) all or a part of the nucleic acid sequence corresponding to the spatial barcode, or a complement thereof, are described herein or are known in the art.

In some embodiments, the tissue to be resected is or comprises a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein).

In some embodiments, the tissue to be resected can include a tumor (e.g., a malignant tumor) of any of the types of cancer describes herein.

In some embodiments, the analyte is a tumor biomarker. In some embodiments, the analyte is a tumor antigen. Exemplary tumor antigens include, but are not limited to, any of the exemplary tumor antigens described herein.

In some embodiments, the tissue to be resected is or comprises an infected tissue, a necrotic tissue, or a diseased tissue. In some embodiments, the analyte can be associated with an infection, necrosis, inflammation, or disease. Non-limiting examples of such analytes are known in the art.

In some embodiments, the tissue to be resected is infected by a bacterium (e.g., any of the exemplary bacteria described herein), a parasite or protozoa (e.g., any of the exemplary parasites or protozoa described herein), a fungus (e.g., any of the exemplary fungi described herein), or a virus (e.g., any of the exemplary viruses described herein).

In some embodiments, the methods provided herein comprise comparing the presence of the analyte at the location in the tissue sample to the presence of the analyte at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the analyte at the location in the tissue sample is significantly different from the presence of the analyte at the different location(s) in the tissue. In some embodiments, the presence of the analyte at the location in the tissue sample is significantly greater than the presence of the analyte at the different location(s) in the tissue sample. In some embodiments, the presence of the analyte at the location in the tissue sample is significantly less than the presence of the analyte at the different location(s) in the tissue sample.

In some embodiments, the location at the tissue sample is determined to be resected if the presence of the analyte at the location in the tissue sample is significantly different from the presence of the analyte at the different location(s). In some embodiments, the location at the tissue sample is determined to be resected if the presence of the analyte at the location in the tissue sample is significantly greater than the presence of the analyte at the different location(s). In some embodiments, the location at the tissue sample is determined to be resected if the presence of the analyte at the location in the tissue sample is significantly less than the presence of the analyte at the different location(s).

In some embodiments, the presence of the analyte at the location in the tissue sample is about 0.1-fold to about 100-fold (e.g., or any of the subranges of this range described herein) greater than the presence of the analyte at the different location(s).

In some embodiments, the presence of the analyte at the location in the tissue sample is about 1% to about 99% (e.g., or any of the subranges of this range described herein) decreased than the presence of the analyte at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of tissue to be resected.

In some embodiments, the method further comprises comparing presence of one or more additional analyte(s) at the location in the tissue sample with the presence of the one or more additional analyte(s) at the different location(s) in the tissue sample. In some embodiments, the presence of a total of about 1 to about 20,000 (e.g., or any of the subranges of this range described herein) analyte(s) at the location are compared to the presence of the analyte(s) at the different location(s).

In some embodiments of any one of the methods described herein, mutant cells are identified according to the presence of the one or more analyte(s) at the location in the tissue sample. In some embodiments, a mutant cell is identified according to the presence of one or more biomarkers described herein. In some embodiments, a mutant cell is identified according to the presence of one or more cell-surface biomarkers, e.g., a cell-surface receptor, at the location in the tissue sample.

In some embodiments, a cell within a location at the tissue sample is identified as a mutant cell if the presence of the one or more analyte(s) at the location in the tissue sample are significantly different from the presence of the analyte(s) at the different location(s). In some embodiments, a cell within a location at the tissue sample is identified as a mutant cell if the presence of the one or more analyte(s) at the location in the tissue sample are significantly greater than the presence of the analyte(s) at the different location(s). In some embodiments, the mutant cell(s) within the location at the tissue sample is determined to be resected if the presence of the analyte(s) at the location in the tissue sample are significantly less than the presence of the analyte at the different location(s).

In some embodiments, a location at the tissue sample comprises about 1 to about 100,000 cells.

The spatial barcode of the capture probe can be any spatial barcode described herein.

In some embodiments of any of the methods described herein, the array can be any of the types of arrays described herein. For example, the array comprises a slide. In some embodiments, the capture probe is attached to the slide (e.g., by its 5' end).

In some embodiments of any of the methods described herein, the array is a bead array. In some embodiments, a 5' end of the capture probe is attached to a bead of the bead array.

In some embodiments of any of the methods described herein, the method comprises extending a 3' end of the capture probe using the specifically bound analyte or analyte binding agent barcode as a template to generate an extended capture probe.

In some embodiments, additional methods are used in combination with the methods described herein to determine the site and size of the tissue to be resected in a subject. In some embodiments, medical imaging modalities such as computed tomography (CT) and magnetic resonance imaging (MRI) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., MRI, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy sample from the subject).

In some embodiments of any of the methods described herein, at least a portion of the tissue to be resected includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the tissue to be resected includes one or more of cancer cell(s), pre-cancerous cell(s), necrotic cell(s), infected cell(s), and disease tissue.

In some embodiments, the tissue resection is considered successful when less than 20%, less than 15%, less than 10%, less than 5%, or zero cancer cell(s), pre-cancerous cell(s), necrotic cell(s), infected cell(s), and/or diseased tissue are detected post-resection as compared to the identified cancer cell(s), pre-cancerous cell(s), necrotic cell(s), infected cell(s), and/or diseased tissue prior to the resection.

In some embodiments of any of the methods described herein, the surgical margin can be the margin between the location(s) of one or more of cancer cell(s), pre-cancerous cell(s), necrotic cell(s), infected cell(s), and disease tissue, and the location(s) of healthy or normal tissue, in a subject.

(d) Methods of Reducing the Risk of Re-Excision of a Tissue

Also provided herein are methods of reducing the risk of re-excision of a tissue from a subject that include: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to the presence of the analyte at different location(s) in the tissue sample, and determining the surgical margin based on the comparison and (d) resecting tissue from the subject using the surgical margin determined in step (c), wherein the method results in a reduction in the risk of future re-excision of the tissue in the subject.

Also provided herein are methods of reducing the risk of re-excision of a tissue from a subject, the method comprising: resecting tissue from the subject using a surgical margin previously determined using a method comprising the steps of: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin based on the comparison.

For example, when a clinician practices the method, the data obtained can provide the clinician with guidance on where to resect the tissue margins thereby reducing the probability that an additional resection might be needed; the clinician will be more confident in capturing tissue margins for a more complete resection. In some embodiments, the analyte is a DNA or RNA. In some embodiments, the analyte is a messenger RNA (mRNA) molecule. In some embodiments, the analyte is a genomic DNA. In some embodiments, the analyte comprises a full-length sequence of a biomarker described herein. In some embodiments, the analyte comprises a fragment of the sequence of a biomarker described herein. In some embodiments of any of the methods described herein, each of the plurality of capture probes comprises (i) a capture domain that binds specifically to an analyte of the tissue sample and (ii) a spatial barcode. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the sequence of the analyte of the tissue sample. In some embodiments, the capture domain can have a total of about 10 nucleotides to about 125 nucleotides (or any of the subranges of this range described herein). In some embodiments, the sequence that is substantially complementary to a portion of the sequence of the analyte can be a random sequence. In some embodiments, the sequence that is substantially complementary to a portion of the sequence of the analyte can include a poly(T) oligonucleotide sequence (e.g., at least 5 contiguous Ts, at least 10 contiguous Ts, or at least 15 contiguous Ts).

In some embodiments of any of the methods described herein, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to all or a part of the extended capture probe. Non-limiting methods for determining the sequence of (i) all or a part of the sequence of the target nucleic acid, or a complement thereof, or (ii) all or a part of the nucleic acid sequence corresponding to the spatial barcode, or a complement thereof, are described herein or are known in the art.

Also provided herein are methods of reducing the risk of re-excision of a tissue from a subject that include: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin based on the comparison; and (e) resecting tissue from the subject using the surgical margin determined in step (d), where the method results in a reduction in the risk of future re-excision of the tissue in the subject. In some embodiments, the analyte is a protein.

Also provided herein are methods of reducing the risk of re-excision of a tissue from a subject, the method comprising: resecting tissue from the subject using a surgical margin previously determined using a method comprising the steps of: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to the presence of the analyte at different location(s) in the tissue sample, and determining the surgical margin based on the comparison.

In some embodiments, the analyte is a full-length protein. In some embodiments, the analyte is a fragment of a protein. In some embodiments, the analyte is a byproduct of a protein. In some embodiments, the protein is any of the exemplary cancer biomarkers described herein.

In some embodiments of any of the methods described herein, each of the plurality of analyte capture agents comprises an analyte binding moiety barcode, an analyte capture sequence, and an analyte binding moiety that binds specifically to an analyte. In some embodiments, the analyte binding moiety is an antibody or an antigen-binding antibody fragment (e.g., a Fab). Any other suitable protein binding moiety known in the art can also be used as an analyte binding moiety. In some embodiments, the analyte binding moiety barcode can be any barcode described herein. In some embodiments, the analyte capture sequence can be any analyte capture sequence described herein. In some embodiments of any of the methods described herein, each of the plurality of capture probes comprises a spatial barcode and a capture domain that binds specifically to the analyte capture sequence. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the analyte capture sequence. In some embodiments, the capture domain can have a total of about 10 nucleotides to about 125 nucleotides (or any of the subranges of this range described herein). In some embodiments, the sequence that is substantially complementary to a portion of the analyte capture sequence can be a random sequence. In some embodiments, the sequence that is substantially complementary to a portion of the analyte capture sequence can include a poly(T) oligonucleotide sequence (e.g., at least 5 contiguous Ts, at least 10 contiguous Ts, or at least 15 contiguous Ts).

In some embodiments, the determining of the sequence is by sequencing. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound analyte capture sequence as a template, and generating a single-stranded nucleic acid comprising a sequence that is complementary to all or a part of the extended capture probe. Non-limiting methods for determining the sequence of (i) all or a part of the nucleic acid sequence corresponding to the analyte binding moiety barcode, or a complement thereof, or (ii) all or a part of the nucleic acid sequence corresponding to the spatial barcode, or a complement thereof, are described herein or are known in the art.

In some embodiments, the resected tissue is or comprises a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein).

In some embodiments, the resected tissue can include a tumor (e.g., a malignant tumor) of any of the types of cancer describes herein.

In some embodiments, the analyte is a tumor biomarker. In some embodiments, the analyte is a tumor antigen. Exemplary tumor antigens include, but are not limited to, any of the exemplary tumor antigens described herein.

In some embodiments, the resected tissue is or comprises an infected tissue, a necrotic tissue, or a diseased tissue. In some embodiments, the analyte can be associated with an infection, necrosis, inflammation, or disease. Non-limiting examples of such analytes are known in the art.

In some embodiments, the resected tissue is infected by a bacterium (e.g., any of the exemplary bacteria described herein), a parasite or protozoa (e.g., any of the exemplary parasites or protozoa described herein), a fungus (e.g., any of the exemplary fungi described herein), or a virus (e.g., any of the exemplary viruses described herein).

In some embodiments, the methods provided herein comprise comparing the presence of the analyte at the location in the tissue sample to presence of the analyte at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the analyte at the location in the tissue sample is significantly different from the presence of the analyte at the different location(s) in the tissue. In some embodiments, the presence of the analyte at the location in the tissue sample is significantly greater than the presence of the analyte at the different location(s) in the tissue sample. In some embodiments, the presence of the analyte at the location in the tissue sample is significantly less than the presence of the analyte at the different location(s) in the tissue sample.

In some embodiments, the location at the tissue sample is determined to be resected if the presence of the analyte at the location in the tissue sample is significantly different from the presence of the analyte at the different location(s). In some embodiments, the location at the tissue sample is determined to be resected if the presence of the analyte at the location in the tissue sample is significantly greater than the presence of the analyte at the different location(s). In some embodiments, the location at the tissue sample is determined to be resected if the presence of the analyte at the location in the tissue sample is significantly less than the presence of the analyte at the different location(s).

In some embodiments, the presence of the analyte at the location in the tissue sample is about 0.1-fold to about 100-fold (e.g., or any of the subranges of this range described herein) greater than the presence of the analyte at the different location(s).

In some embodiments, the presence of the analyte at the location in the tissue sample is about 1% to about 99% (e.g., or any of the subranges of this range described herein) decreased than the presence of the analyte at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of tissue to be resected.

In some embodiments, the method further comprises comparing the presence of one or more additional analyte(s) at the location in the tissue sample with the presence of the one or more additional analyte(s) at the different location(s) in the tissue sample. In some embodiments, the presence of a total of about 1 to about 20,000 (e.g., or any of the subranges of this range described herein) analyte(s) at the location are compared to the presence of the analyte(s) at the different location(s).

In some embodiments of any one of the methods described herein, mutant cells are identified according to the presence of the one or more analyte(s) at the location in the tissue sample. In some embodiments, a mutant cell is identified according to the presence of one or more biomarkers described herein. In some embodiments, a mutant cell is identified according to the presence of one or more cell-surface biomarkers, e.g., a cell-surface receptor, at the location in the tissue sample.

In some embodiments, a cell within a location at the tissue sample is identified as a mutant cell if the presence of the one or more analyte(s) at the location in the tissue sample are significantly different from the presence of the analyte(s) at the different location(s). In some embodiments, a cell within a location at the tissue sample is identified as a mutant cell if the presence of the one or more analyte(s) at the location in the tissue sample are significantly greater than the presence of the analyte(s) at the different location(s). In some embodiments, the mutant cell(s) within the location at the tissue sample is determined to be resected if the presence of the analyte(s) at the location in the tissue sample are significantly less than the presence of the analyte at the different location(s).

In some embodiments, a location at the tissue sample comprises about 1 to about 100,000 cells.

The spatial barcode of the capture probe can be any spatial barcode described herein.

In some embodiments of any of the methods described herein, the array can be any of the types of arrays described herein. For example, the array comprises a slide. In some embodiments, the capture probe is attached to the slide (e.g., by its 5' end).

In some embodiments of any of the methods described herein, the array is a bead array. In some embodiments, a 5' end of the capture probe is attached to a bead of the bead array.

In some embodiments of any of the methods described herein, the method comprises extending a 3' end of the capture probe using the specifically bound analyte or analyte binding agent barcode as a template to generate an extended capture probe.

In some embodiments, additional methods are used in combination with the methods described herein to determine the site and size of the tissue to be resected in a subject. In some embodiments, medical imaging modalities such as computed tomography (CT) and magnetic resonance imaging (MRI) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., MRI, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy sample from the subject).

In some embodiments of any of the methods described herein, at least a portion of the resected tissue includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the resected tissue includes one or more of cancer cell(s), pre-cancerous cell(s), necrotic cell(s), infected cell(s), and disease tissue.

In some embodiments of any of the methods described herein, the surgical margin can be the margin between the location(s) of one or more of cancer cell(s), pre-cancerous cell(s), necrotic cell(s), infected cell(s), and disease tissue, and the location(s) of healthy or normal tissue, in a subject.

In some embodiments, the methods described herein are more accurate in determining the surgical margin of a tissue to be resected than the traditional methods, such as medical imaging or scanning methods.

In some embodiments, a re-excision includes additional tissue excisions during the initial surgical procedure to obtain the tissue sample. In some embodiments, a re-excision includes additional tissue excisions during a future procedure.

In some embodiments, the methods described herein results in a reduction (e.g., at least a 5% reduction, at least a 10% reduction, at least a 15% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, or at least a 99% reduction, or about a 1% to about a 5% reduction, about a 5% to about a 10% reduction, about a 10% to about a 99% reduction, about a 10% to about a 90% reduction, about a 10% to about a 80% reduction, about a 10% to about a 70% reduction, about a 10% to about a 60% reduction, about a 10% to about a 50% reduction, about a 10% to about a 40% reduction, about a 10% to about a 30% reduction, about a 10% to about a 20% reduction, about a 10% to about a 15% reduction, about a 20% to about a 99% reduction, about a 20% to about a 90% reduction, about a 20% to about a 80% reduction, about a 20% to about a 70% reduction, about a 20% to about a 60% reduction, about a 20% to about a 50% reduction, about a 20% to about a 40% reduction, about a 20% to about a 30% reduction, about a 30% to about a 99% reduction, about a 30% to about a 90% reduction, about a 30% to about a 80% reduction, about a 30% to about a 70% reduction, about a 30% to about a 60% reduction, about a 30% to about a 50% reduction, about a 30% to about a 40% reduction, about a 40% to about a 99% reduction, about a 40% to about a 90% reduction, about a 40% to about a 80% reduction, about a 40% to about a 70% reduction, about a 40% to about a 60% reduction, about a 40% to about a 50% reduction, about a 50% to about a 99% reduction, about a 50% to about a 90% reduction, about a 50% to about a 50% to about a 80% reduction, about a 50% to about a 70% reduction, about a 50% to about a 65% reduction, about a 50% to about a 60% reduction, about a 50% to about a 55% reduction, about a 60% to about a 99% reduction, about a 60% to about a 90% reduction, about a 60% to about a 80% reduction, about a 60% to about a 75% reduction, about a 60% to about a 70% reduction, about a 60% to about a 65% reduction, about a 70% to about a 99% reduction, about a 70% to about a 95% reduction, about a 70% to about a 90% reduction, about a 70% to about a 85% reduction, about a 70% to about a 80% reduction, about a 70% to about a 75% reduction, about a 80% to about a 99% reduction, about a 80% to about a 95% reduction, about a 80% to about a 90% reduction, about a 80% to about a 85% reduction, about a 90% to about a 99% reduction, about a 90% to about a 95% reduction, or about a 95% to about a 99% reduction) in the risk of future re-excision of the tissue in the subject (e.g., as a compared to a similar subject that has undergone resection based on an imaging method or by the physician's visual assessment during resection).

Figure 4:
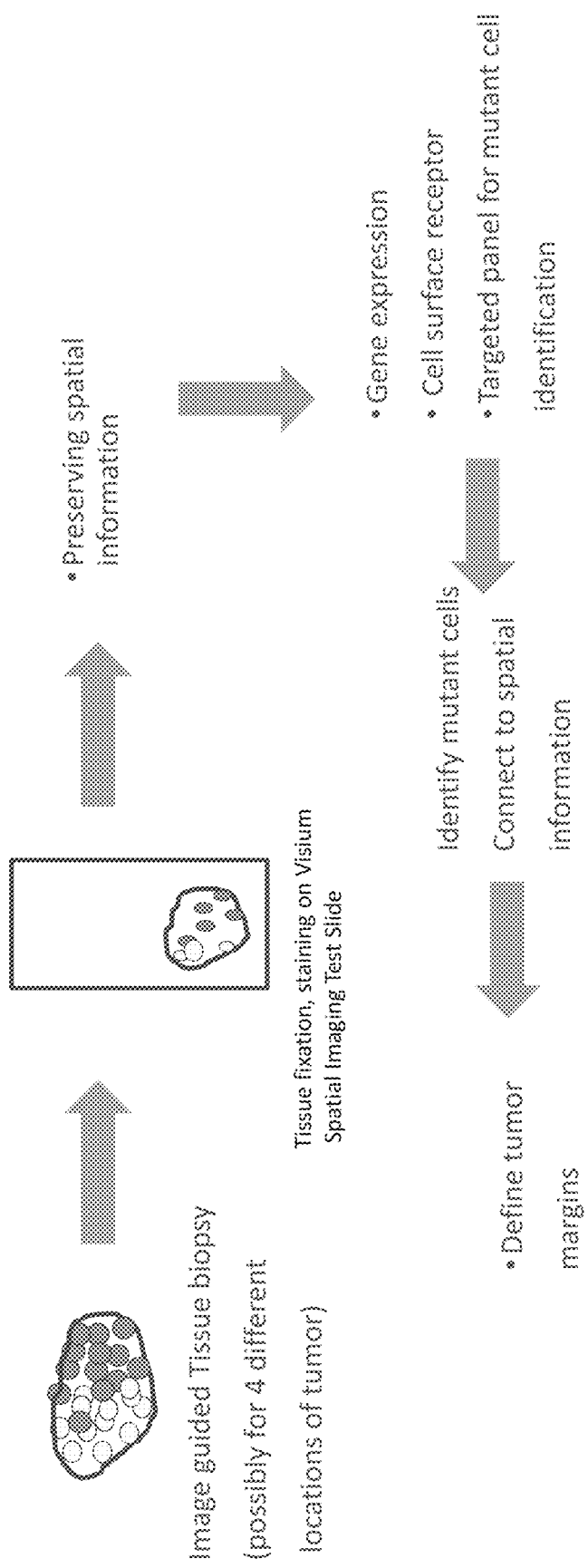
FIG. 4 is a schematic showing an exemplary method of determining a surgical margin (e.g., a tumor margin) of a tissue to be resected from a subject.

A non-limiting example of a method for identifying a surgical margin of a tissue to be resected is depicted in FIG. 4. Briefly, a biopsy tissue is excised from a subject and imaged for potential tumor tissue cells or other disease related cells. After imaging, the tissue is sectioned and one or more sections of tissue are subjected to the methods described herein for spatial determination and location of cells of interest in a tissue. For example, gene expression along the margins of a tissue section indicative of cancer or a disease state and/or the location of receptors along the margins of a tissue section indicative of cancer or a disease state is determined via a spatial array. Additionally, known mutations associated with a cancer or disease state can be spatially identified along the margins of a tissue section. Gene expression analysis and/or receptor presence and/or mutational state of cells within the tissue margins can be used to determine whether a surgeon has sufficiently resected the tissue. For example, the presence of one or more genes, receptors and/or mutations indicative of a cancer or disease state in a spatially analyzed tissue margin section would indicate that the resection of the cancerous or diseased tissue was not complete as such a more expanded resection might be necessary. When the tissue section margins are absent of those biomarkers that were used to indicate a cancer or disease state, then a resection could be considered successful for that location.

(e) Methods of Reducing the Rate of Recurrence of a Tissue Abnormality

Provided herein are methods of reducing the rate of recurrence of a tissue abnormality in a subject that include: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin based on the comparison; (d) resecting tissue from the subject using the surgical margin determined in step (c), wherein the method results in a reduction in the rate of recurrence of a tissue abnormality in the subject.

Also provided herein are methods of reducing the rate of recurrence of a tissue abnormality in a subject, the method comprising: resecting tissue from the subject using a surgical margin previously determined using a method comprising the steps of: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to the presence of the analyte at different location(s) in the tissue sample, and determining the surgical margin based on the comparison.

For example, the methods described herein allow a clinician to identify tissue tumor margins with confidence such that tissue resection will increase the likelihood that the complete tumor or tissue abnormality has been removed from the subject, thereby reducing the rate of recurrence of the abnormal tissue or tumor in the subject.

In some embodiments, the analyte is a DNA or RNA. In some embodiments, the analyte is a messenger RNA (mRNA) molecule. In some embodiments, the analyte is a genomic DNA. In some embodiments, the analyte comprises a full-length sequence of a biomarker described herein. In some embodiments, the analyte comprises a fragment of the sequence of a biomarker described herein. In some embodiments of any of the methods described herein, each of the plurality of capture probes comprises (i) a capture domain that binds specifically to an analyte of the tissue sample and (ii) a spatial barcode. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the sequence of the analyte of the tissue sample. In some embodiments, the capture domain can have a total of about 10 nucleotides to about 125 nucleotides (or any of the subranges of this range described herein). In some embodiments, the sequence that is substantially complementary to a portion of the sequence of the analyte can be a random sequence. In some embodiments, the sequence that is substantially complementary to a portion of the sequence of the analyte can include a poly(T) oligonucleotide sequence (e.g., at least 5 contiguous Ts, at least 10 contiguous Ts, or at least 15 contiguous Ts).

In some embodiments of any of the methods described herein, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to all or a part of the extended capture probe. Non-limiting methods for determining the sequence of (i) all or a part of the sequence of the target nucleic acid, or a complement thereof, or (ii) all or a part of the nucleic acid sequence corresponding to the spatial barcode, or a complement thereof, are described herein or are known in the art.

Also provided herein are methods of reducing the rate of recurrence of a tissue abnormality in a subject that include: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin based on the comparison; and (e) resecting tissue from the subject using the surgical margin determined in step (d), where the method results in a reduction in the rate of recurrence of a tissue abnormality in the subject.

Also provided herein are methods of reducing the rate of recurrence of a tissue abnormality in a subject, the method comprising: resecting tissue from the subject using a surgical margin previously determined using a method comprising the steps of: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing the presence of the analyte at the location in the tissue sample to presence of the analyte at different location(s) in the tissue sample, and determining the surgical margin based on the comparison.

In some embodiments, the analyte is a protein. In some embodiments, the analyte is a full-length protein. In some embodiments, the analyte is a fragment of a protein. In some embodiments, the analyte is a byproduct of a protein. In some embodiments, the protein is any of the exemplary cancer biomarkers described herein.

In some embodiments of any of the methods described herein, each of the plurality of analyte capture agents comprises an analyte binding moiety barcode, an analyte capture sequence, and an analyte binding moiety that binds specifically to an analyte. In some embodiments, the analyte binding moiety is an antibody or an antigen-binding antibody fragment (e.g., a Fab). Any other suitable protein binding moiety known in the art can also be used as an analyte binding moiety. In some embodiments, the analyte binding moiety barcode can be any barcode described herein. In some embodiments, the analyte capture sequence can be any analyte capture sequence described herein. In some embodiments of any of the methods described herein, each of the plurality of capture probes comprises a spatial barcode and a capture domain that binds specifically to the analyte capture sequence. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the analyte capture sequence. In some embodiments, the capture domain can have a total of about 10 nucleotides to about 125 nucleotides (or any of the subranges of this range described herein). In some embodiments, the sequence that is substantially complementary to a portion of the analyte capture sequence can be a random sequence. In some embodiments, the sequence that is substantially complementary to a portion of the analyte capture sequence can include a poly(T) oligonucleotide sequence (e.g., at least 5 contiguous Ts, at least 10 contiguous Ts, or at least 15 contiguous Ts).

In some embodiments, the determining of the sequence is by sequencing. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound analyte capture sequence as a template, and generating a single-stranded nucleic acid comprising a sequence that is complementary to all or a part of the extended capture probe. Non-limiting methods for determining the sequence of (i) all or a part of the nucleic acid sequence corresponding to the analyte binding moiety barcode, or a complement thereof, or (ii) all or a part of the nucleic acid sequence corresponding to the spatial barcode, or a complement thereof, are described herein or are known in the art.

In some embodiments, an abnormality in the resected tissue is or comprises a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein).

In some embodiments, the resected tissue can include a tumor, e.g., a tumor (e.g., a malignant tumor) of any of the types of cancer describes herein.

In some embodiments, the analyte is a tumor biomarker. In some embodiments, the analyte is a tumor antigen. Exemplary tumor antigens include, but are not limited to, any of the exemplary tumor antigens described herein.

In some embodiments, the resected tissue is or comprises an infected tissue, a necrotic tissue, or a diseased tissue. In some embodiments, the analyte can be associated with an infection, necrosis, inflammation, or disease. Non-limiting examples of such analytes are known in the art.

In some embodiments, the resected tissue is infected by a bacterium (e.g., any of the exemplary bacteria described herein), a parasite or protozoa (e.g., any of the exemplary parasites or protozoa described herein), a fungus (e.g., any of the exemplary fungi described herein), or a virus (e.g., any of the exemplary viruses described herein).

In some embodiments, the methods provided herein comprise comparing the presence of the analyte at the location in the tissue sample to presence of the analyte at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the analyte at the location in the tissue sample is significantly different from the presence of the analyte at the different location(s) in the tissue. In some embodiments, the presence of the analyte at the location in the tissue sample is significantly greater than the presence of the analyte at the different location(s) in the tissue sample. In some embodiments, the presence of the analyte at the location in the tissue sample is significantly less than the presence of the analyte at the different location(s) in the tissue sample.

In some embodiments, the location at the tissue sample is determined to be resected if the presence of the analyte at the location in the tissue sample is significantly different from the presence of the analyte at the different location(s). In some embodiments, the location at the tissue sample is determined to be resected if the presence of the analyte at the location in the tissue sample is significantly greater than the presence of the analyte at the different location(s). In some embodiments, the location at the tissue sample is determined to be resected if the presence of the analyte at the location in the tissue sample is significantly less than the presence of the analyte at the different location(s).

In some embodiments, the presence of the analyte at the location in the tissue sample is about 0.1-fold to about 100-fold (e.g., or any of the subranges of this range described herein) greater than the presence of the analyte at the different location(s).

In some embodiments, the presence of the analyte at the location in the tissue sample is about 1% to about 99% (e.g., or any of the subranges of this range described herein) decreased than the presence of the analyte at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of tissue to be resected.

In some embodiments, the method further comprises comparing presence of one or more additional analyte(s) at the location in the tissue sample with the presence of the one or more additional analyte(s) at the different location(s) in the tissue sample. In some embodiments, the presence of a total of about 1 to about 20,000 (e.g., or any of the subranges of this range described herein) analyte(s) at the location are compared to the presence of the analyte(s) at the different location(s).

In some embodiments of any one of the methods described herein, mutant cells are identified according to the presence of the one or more analyte(s) at the location in the tissue sample. In some embodiments, a mutant cell is identified according to the presence of one or more biomarkers described herein. In some embodiments, a mutant cell is identified according to the presence of one or more cell-surface biomarkers, e.g., a cell-surface receptor, at the location in the tissue sample.

In some embodiments, a cell within a location at the tissue sample is identified as a mutant cell if the presence of the one or more analyte(s) at the location in the tissue sample are significantly different from the presence of the analyte(s) at the different location(s). In some embodiments, a cell within a location at the tissue sample is identified as a mutant cell if the presence of the one or more analyte(s) at the location in the tissue sample are significantly greater than the presence of the analyte(s) at the different location(s). In some embodiments, the mutant cell(s) within the location at the tissue sample is determined to be resected if the presence of the analyte(s) at the location in the tissue sample are significantly less than the presence of the analyte at the different location(s).

In some embodiments, a location at the tissue sample comprises about 1 to about 100,000 cells.

The spatial barcode of the capture probe can be any spatial barcode described herein.

In some embodiments of any of the methods described herein, the array can be any of the types of arrays described herein. For example, the array comprises a slide. In some embodiments, the capture probe is attached to the slide (e.g., by its 5' end).

In some embodiments of any of the methods described herein, the array is a bead array. In some embodiments, a 5' end of the capture probe is attached to a bead of the bead array.

In some embodiments of any of the methods described herein, the method comprises extending a 3' end of the capture probe using the specifically bound analyte or analyte binding agent barcode as a template to generate an extended capture probe.

In some embodiments, additional methods are used in combination with the methods described herein to determine the site and size of the tissue to be resected in a subject. In some embodiments, medical imaging modalities such as computed tomography (CT) and magnetic resonance imaging (Mill) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., Mill, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy sample from the subject).

In some embodiments of any of the methods described herein, at least a portion of the resected tissue includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the resected tissue includes one or more of cancer cell(s), pre-cancerous cell(s), necrotic cell(s), infected cell(s), and disease tissue.

In some embodiments of any of the methods described herein, the surgical margin can be the margin between the location(s) of one or more of cancer cell(s), pre-cancerous cell(s), necrotic cell(s), infected cell(s), and disease tissue, and the location(s) of healthy or normal tissue, in a subject.

In some embodiments, the methods described herein results in a reduction (e.g., at least a 5% reduction, at least a 10% reduction, at least a 15% reduction, at least a 20% reduction, at least a 25% reduction, at least a 30% reduction, at least a 35% reduction, at least a 40% reduction, at least a 45% reduction, at least a 50% reduction, at least a 55% reduction, at least a 60% reduction, at least a 65% reduction, at least a 70% reduction, at least a 75% reduction, at least a 80% reduction, at least a 85% reduction, at least a 90% reduction, at least a 95% reduction, or at least a 99% reduction, or about a 1% to about a 99% reduction (e.g., or any of the subranges of this range described herein) in the rate of recurrence of a tissue abnormality (e.g., any of the cancers described herein) in the subject (e.g., as a compared to a similar subject that has undergone resection based on an imaging method or by the physician's visual assessment during resection).

(f) Methods of Treating a Subject by Excising or Avoiding Excision of a Nerve or Blood Vessel Also provided herein are methods of treating a subject that include: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin based on the comparison; and (d) excising a nerve or blood vessel that is within the determined surgical margin in the subject, or avoiding excision of a nerve or blood vessel outside of the determined surgical margin in the subject.

Also provided herein are methods of treating a subject, the method comprising: excising a nerve or blood vessel that is within a surgical margin in the subject, or avoiding excision of a nerve or blood vessel outside of the surgical margin in the subject, wherein the surgical margin was previously determined using a method comprising the steps of: (a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode; (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (c) comparing the presence of the analyte at the location in the tissue sample to presence of the analyte at different location(s) in the tissue sample, and determining the surgical margin based on the comparison.

For example, when a clinician practices the method, the data obtained can provide the clinician with information of the accurate location of the cancerous or diseased tissue, therefore provide the accurate surgical margin of the tissue to be resected. Using the information of the accurate surgical margin provided by the method described herein, the clinician is able to achieve, e.g., more complete and accurate excision, thereby treating the subject in need thereof.

In some embodiments, the analyte is a DNA or RNA. In some embodiments, the analyte is a messenger RNA (mRNA) molecule. In some embodiments, the analyte is a genomic DNA. In some embodiments, the analyte comprises a full-length sequence of a biomarker described herein. In some embodiments, the analyte comprises a fragment of the sequence of a biomarker described herein. In some embodiments of any of the methods described herein, each of the plurality of capture probes comprises (i) a capture domain that binds specifically to an analyte of the tissue sample and (ii) a spatial barcode. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the sequence of the analyte of the tissue sample. In some embodiments, the capture domain can have a total of about 10 nucleotides to about 125 nucleotides (or any of the subranges of this range described herein). In some embodiments, the sequence that is substantially complementary to a portion of the sequence of the analyte can be a random sequence. In some embodiments, the sequence that is substantially complementary to a portion of the sequence of the analyte can include a poly(T) oligonucleotide sequence (e.g., at least 5 contiguous Ts, at least 10 contiguous Ts, or at least 15 contiguous Ts).

In some embodiments of any of the methods described herein, step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to all or a part of the extended capture probe. Non-limiting methods for determining the sequence of (i) all or a part of the sequence of the target nucleic acid, or a complement thereof, or (ii) all or a part of the nucleic acid sequence corresponding to the spatial barcode, or a complement thereof, are described herein or are known in the art.

Also provided herein are methods of treating a subject that include: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing presence of the analyte at the location in the tissue sample to presence of the analyte at different location(s) in the tissue sample, and determining the surgical margin based on the comparison; and (e) excising a nerve or blood vessel that is within the determined surgical margin in the subject, or avoiding excision of a nerve or blood vessel outside of the determined surgical margin in the subject.

Also provided herein are methods of treating a subject, the method comprising: excising a nerve or blood vessel that is within a surgical margin in the subject, or avoiding excision of a nerve or blood vessel outside of the surgical margin in the subject, wherein the surgical margin was previously determined using a method comprising the steps of: (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte; (b) disposing the tissue sample onto an array, wherein the array comprises a plurality of capture probes, wherein a capture probe of the plurality of capture probes comprises a spatial barcode and a capture domain that binds specifically to the analyte capture sequence; (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample; (d) comparing presence of the analyte at the location in the tissue sample to presence of the analyte at different location(s) in the tissue sample, and determining the surgical margin based on the comparison.

In some embodiments, the analyte is a protein. In some embodiments, the analyte is a full-length protein. In some embodiments, the analyte is a fragment of a protein. In some embodiments, the analyte is a byproduct of a protein. In some embodiments, the protein is any of the exemplary cancer biomarkers described herein.

In some embodiments of any of the methods described herein, each of the plurality of analyte capture agents comprises an analyte binding moiety barcode, an analyte capture sequence, and an analyte binding moiety that binds specifically to an analyte. In some embodiments, the analyte binding moiety is an antibody or an antigen-binding antibody fragment (e.g., a Fab). Any other suitable protein binding moiety known in the art can also be used as an analyte binding moiety. In some embodiments, the analyte binding moiety barcode can be any barcode described herein. In some embodiments, the analyte capture sequence can be any analyte capture sequence described herein. In some embodiments of any of the methods described herein, each of the plurality of capture probes comprises a spatial barcode and a capture domain that binds specifically to the analyte capture sequence. The capture probe can be any capture probe described herein. In some embodiments, the capture domain of the capture probe comprises a sequence that is substantially complementary (e.g., at least 80%, at least 85%, at least 90%, at least 95%, at least 99%, or 100% complementary) to a portion of the analyte capture sequence. In some embodiments, the capture domain can have a total of about 10 nucleotides to about 125 nucleotides (or any of the subranges of this range described herein). In some embodiments, the sequence that is substantially complementary to a portion of the analyte capture sequence can be a random sequence. In some embodiments, the sequence that is substantially complementary to a portion of the analyte capture sequence can include a poly(T) oligonucleotide sequence (e.g., at least 5 contiguous Ts, at least 10 contiguous Ts, or at least 15 contiguous Ts).

In some embodiments, the determining of the sequence is by sequencing. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound analyte capture sequence as a template, and generating a single-stranded nucleic acid comprising a sequence that is complementary to all or a part of the extended capture probe. Non-limiting methods for determining the sequence of (i) all or a part of the nucleic acid sequence corresponding to the analyte binding moiety barcode, or a complement thereof, or (ii) all or a part of the nucleic acid sequence corresponding to the spatial barcode, or a complement thereof, are described herein or are known in the art.

In some embodiments, the tissue to be resected is or comprises a tumor (e.g., a malignant or a benign tumor). In some embodiments, the tumor is a solid tumor. In some embodiments, the subject is suspected of having a cancer. In some embodiments, the subject has been previously diagnosed or identified as having a cancer (e.g., any of the exemplary cancers described herein).

In some embodiments, the tissue to be resected can include a tumor (e.g., a malignant tumor) of any of the types of cancer describes herein.

In some embodiments, the analyte is a tumor biomarker. In some embodiments, the analyte is a tumor antigen. Exemplary tumor antigens include, but are not limited to, any of the exemplary tumor antigens described herein.

In some embodiments, the tissue to be resected is or comprises an infected tissue, a necrotic tissue, or a diseased tissue. In some embodiments, the analyte can be associated with an infection, necrosis, inflammation, or disease. Non-limiting examples of such analytes are known in the art.

In some embodiments, the tissue to be resected is infected by a bacterium (e.g., any of the exemplary bacteria described herein), a parasite or protozoa (e.g., any of the exemplary parasites or protozoa described herein), a fungus (e.g., any of the exemplary fungi described herein), or a virus (e.g., any of the exemplary viruses described herein).

In some embodiments, the methods provided herein comprise comparing the presence of the analyte at the location in the tissue sample to presence of the analyte at different location(s) in the tissue sample, and determining the size and site of a tissue to be resected from the subject based on the comparison. In some embodiments, the different location(s) in the tissue sample are reference location(s). In some embodiments, the reference location(s) in the tissue sample are locations of healthy tissue. In some embodiments, the reference location(s) in the tissue sample are locations of non-cancerous tissue. In some embodiments, the reference location(s) in the tissue sample are locations of non-tumor tissue. In some embodiments, the reference location(s) in the tissue sample are locations with no abnormalities such as tumor, cancer, necrosis, inflammation, infection, or disease.

In some embodiments, the presence of the analyte at the location in the tissue sample is significantly different from the presence of the analyte at the different location(s) in the tissue. In some embodiments, the presence of the analyte at the location in the tissue sample is significantly greater than the presence of the analyte at the different location(s) in the tissue sample. In some embodiments, the presence of the analyte at the location in the tissue sample is significantly less than the presence of the analyte at the different location(s) in the tissue sample.

In some embodiments, the location at the tissue sample is determined to be resected if the presence of the analyte at the location in the tissue sample is significantly different from the presence of the analyte at the different location(s). In some embodiments, the location at the tissue sample is determined to be resected if the presence of the analyte at the location in the tissue sample is significantly greater than the presence of the analyte at the different location(s). In some embodiments, the location at the tissue sample is determined to be resected if the presence of the analyte at the location in the tissue sample is significantly less than the presence of the analyte at the different location(s).

In some embodiments, the presence of the analyte at the location in the tissue sample is about 0.1-fold to about 100-fold (e.g., or any of the subranges of this range described herein) greater than the presence of the analyte at the different location(s).

In some embodiments, the presence of the analyte at the location in the tissue sample is about 1% to about 99% (e.g., or any of the subranges of this range described herein) decreased than the presence of the analyte at the different location(s).

In some embodiments, the presence of certain biomarkers associated with a cancer and/or disease (e.g., breast cancer biomarkers in ductal carcinoma) at a location in a tissue sample are evaluated. If the presence of certain biomarkers associated with a cancer and/or disease are below a threshold value for those biomarkers, the location in the tissue sample is considered "clear." If the presence of certain biomarkers associated with a cancer and/or disease are above a threshold value for those biomarkers, the location in the tissue sample is considered within the margin of nerve and/or blood vessel to be resected.

In some embodiments, the method further comprises comparing presence of one or more additional analyte(s) at the location in the tissue sample with the presence of the one or more additional analyte(s) at the different location(s) in the tissue sample. In some embodiments, the presence of a total of about 1 to about 20,000 (e.g., or any of the subranges of this range described herein) analyte(s) at the location are compared to the presence of the analyte(s) at the different location(s).

In some embodiments of any one of the methods described herein, mutant cells are identified according to the presence of the one or more analyte(s) at the location in the tissue sample. In some embodiments, a mutant cell is identified according to the presence of one or more biomarkers described herein. In some embodiments, a mutant cell is identified according to the presence of one or more cell-surface biomarkers, e.g., a cell-surface receptor, at the location in the tissue sample.

In some embodiments, a cell within a location at the tissue sample is identified as a mutant cell if the presence of the one or more analyte(s) at the location in the tissue sample are significantly different from the presence of the analyte(s) at the different location(s). In some embodiments, a cell within a location at the tissue sample is identified as a mutant cell if the presence of the one or more analyte(s) at the location in the tissue sample are significantly greater than the presence of the analyte(s) at the different location(s). In some embodiments, the mutant cell(s) within the location at the tissue sample is determined to be resected if the presence of the analyte(s) at the location in the tissue sample are significantly less than the presence of the analyte at the different location(s).

In some embodiments, a location at the tissue sample comprises about 1 to about 100,000 cells.

The spatial barcode of the capture probe can be any spatial barcode described herein.

In some embodiments of any of the methods described herein, the array can be any of the types of arrays described herein. For example, the array comprises a slide. In some embodiments, the capture probe is attached to the slide (e.g., by its 5' end).

In some embodiments of any of the methods described herein, the array is a bead array. In some embodiments, a 5' end of the capture probe is attached to a bead of the bead array.

In some embodiments of any of the methods described herein, the method comprises extending a 3' end of the capture probe using the specifically bound analyte or analyte binding agent barcode as a template to generate an extended capture probe.

In some embodiments, additional methods are used in combination with the methods described herein to determine the site and size of the tissue to be resected in a subject. In some embodiments, medical imaging modalities such as computed tomography (CT) and magnetic resonance imaging (MRI) are used in combination with the methods described herein. In some embodiments, a position emission tomography (PET) is used in combination with the methods described herein. For example, an initial scanning of a cancer patient and/or imaging of a tissue sample from a cancer patient can be performed using, e.g., MRI, CT, and/or PET prior to the methods described herein, and a preliminary assessment of a surgical margin can be performed. The initial information can provide guidance on, e.g., where to obtain the tissue sample for use in the methods described herein, the size of the tissue sample, and/or the number of tissue samples needed. In another example, a follow-up scanning and/or imaging can be performed using e.g., MRI, CT, and/or PET after the methods described herein are performed. The follow-up scanning and/or imaging provide information on, e.g., the clearance of the cancerous and/or diseased tissue, and whether there are residual cancerous and/or diseased tissue. Any other suitable methods known in the art can also be used in combination with the methods described herein.

Some embodiments of any of the methods described herein can further include obtaining the tissue sample from the subject (e.g., obtain a biopsy sample from the subject).

In some embodiments of any of the methods described herein, at least a portion of the tissue to be resected includes cancer cell(s), pre-cancerous cell(s), necrotic cell(s), infected cell(s), and/or diseased tissue. In some embodiments, at least 80%, at least 85%, at least 90%, at least 95%, at least 99%, or 100% of the tissue to be resected includes one or more of cancer cell(s), pre-cancerous cell(s), necrotic cell(s), infected cell(s), and disease tissue.

In some embodiments of any of the methods described herein, the surgical margin can be the margin between the location(s) of one or more of cancer cell(s), pre-cancerous cell(s), necrotic cell(s), infected cell(s), and disease tissue, and the location(s) of healthy or normal tissue, in a subject.

In some embodiments, the methods described herein comprise excising a nerve and/or blood vessel that is within the determined surgical margin in the subject. In some embodiments, at least 80%, at least 85%, at least 90%, at least 95%, or at least 99% of the nerve and/or blood vessel that is within the determined surgical margin are excised.

In some embodiments, the excision of a nerve and/or blood vessel is considered successful when less than 20%, less than 15%, less than 10%, less than 5%, or zero nerve and/or blood vessel that is within the determined surgical margin is detected post-excision as compared to the identified nerve and/or blood vessel that is within the determined surgical margin prior to the resection.

In some embodiments, the treatment is considered successful when less than 20%, less than 15%, less than 10%, less than 5%, or zero nerve and/or blood vessel that is within the determined surgical margin is detected post-excision as compared to the identified nerve and/or blood vessel that is within the determined surgical margin prior to the resection.

In some embodiments, the methods described herein comprise avoiding excision of a nerve and/or blood vessel outside of the determined surgical margin in the subject. In some embodiments, no more than 20%, no more than 15%, no more than 10%, no more than 8%, no more than 6%, no more than 4%, no more than 2%, or no more than 1% of the nerve and/or blood vessel outside of the determined surgical margin is excised.

The term "presence" as used herein refers to the existence and/or level(s) of any object(s) (e.g., an analyte) being measured, quantified, and/or compared in any of the methods described herein.

EXEMPLARY EMBODIMENTS

Embodiment 1. A method of determining size and site of a tissue to be resected from a subject, the method comprising:

(a) contacting a tissue sample obtained from the subject to an array comprising a plurality of capture probes, wherein a capture probe of the plurality of capture probes comprises (i) a capture domain that binds specifically to an analyte of the tissue sample and (ii) a spatial barcode;

(b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;

(c) comparing the presence of the analyte at the location in the tissue sample to presence of the analyte at a different location in the tissue sample, and determining the size and site of the tissue to be resected from the subject based on the comparison.

Embodiment 2. The method of Embodiment 1, wherein the tissue to be resected is a tumor.

Embodiment 3. The method of Embodiment 1, wherein the tissue to be resected is infected tissue, necrotic tissue, or diseased tissue.

Embodiment 4. The method of Embodiment 1 or 2, wherein the subject is suspected of or diagnosed as having a cancer.

Embodiment 5. The method of Embodiment 4, wherein the cancer is breast cancer.

Embodiment 6. The method of Embodiment 1, wherein the subject is suspected of or diagnosed as having ductal carcinoma in situ.

Embodiment 7. The method of any one of Embodiments 1-6, wherein the analyte is RNA.

Embodiment 8. The method of Embodiment 7, wherein the RNA is mRNA.

Embodiment 9. The method of any one of Embodiments 1-6, wherein the analyte is DNA.

Embodiment 10. The method of Embodiment 9, wherein the DNA is genomic DNA.

Embodiment 11. The method of any one of Embodiments 1-10, wherein the array comprises a slide having the plurality of capture probes.

Embodiment 12. The method of any one of Embodiments 1-10, wherein the array is a bead array.

Embodiment 13. The method of any one of Embodiments 1-12, wherein step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof.

Embodiment 14. The method of Embodiment 13, wherein the sequencing is high throughput sequencing.

Embodiment 15. The method of any one of Embodiments 1-12, wherein step (b) comprises extending a 3' end of the capture probe using the specifically bound analyte as a template to generate an extended capture probe.

Embodiment 16. The method of Embodiment 15, wherein step (b) further comprises generating a single-stranded nucleic acid comprising a nucleic acid sequence that is complementary to all or a part of the extended capture probe.

Embodiment 17. A method of determining size and site of a tissue to be resected from a subject, the method comprising:

(a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte;

(b) disposing the tissue sample onto an array, wherein the array comprises a plurality of capture probes, wherein a capture probe of the plurality of capture probes comprises a spatial barcode and a capture domain that binds specifically to the analyte capture sequence;

(c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;

(d) comparing the presence of the analyte at the location in the tissue sample to the presence of the analyte at different location(s) in the tissue sample, and determining the size and site of the tissue to be resected from the subject based on the comparison.

Embodiment 18. The method of Embodiment 17, wherein the tissue to be resected is a tumor.

Embodiment 19. The method of Embodiment 17, wherein the tissue to be resected is infected tissue, necrotic tissue, or diseased tissue.

Embodiment 20. The method of Embodiment 17 or 18, wherein the subject is suspected of or diagnosed as having a cancer.

Embodiment 21. The method of Embodiment 20, wherein the cancer is breast cancer.

Embodiment 22. The method of Embodiment 17, wherein the subject is suspected of or diagnosed as having ductal carcinoma in situ.

Embodiment 23. The method of any one of Embodiments 17-22, wherein the analyte is a protein.

Embodiment 24. The method of Embodiment 23, wherein the analyte is an intracellular protein.

Embodiment 25. The method of Embodiment 23, wherein the analyte is an extracellular protein.

Embodiment 26. The method of any one of Embodiments 23-25, wherein the analyte binding moiety is an antibody or an antigen-binding antibody fragment.

Embodiment 27. The method of any one of Embodiments 17-26, wherein the array comprises a slide having the plurality of capture probes.

Embodiment 28. The method of any one of Embodiments 17-26, wherein the array is a bead array.

Embodiment 29. The method of any one of Embodiments 17-28, wherein step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof.

Embodiment 30. The method of Embodiment 29, wherein the sequencing is high throughput sequencing.

Embodiment 31. The method of any one of Embodiments 17-30, wherein step (c) comprises extending a 3' end of the capture probe using the specifically bound analyte capture agent as a template to generate an extended capture probe.

Embodiment 32. The method of Embodiment 31, wherein step (c) further comprises generating a single-stranded nucleic acid comprising a sequence that is complementary to all or a part of the extended capture probe.

Embodiment 33. A method of treating a subject in need thereof, the method comprising:

resecting tissue from the subject using a surgical margin previously determined using a method comprising the steps of:

(a) contacting a tissue sample obtained from the subject to an array comprising a plurality of capture probes, wherein a capture probe of the plurality of capture probes comprises (i) a capture domain that specifically binds to an analyte of the tissue sample and (ii) a spatial barcode;

(b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;

(c) comparing the presence of the analyte at the location in the tissue sample to presence of the analyte at a different location in the tissue sample, and determining the surgical margin based on the comparison.

Embodiment 34. The method of Embodiment 33, wherein the resected tissue is a tumor.

Embodiment 35. The method of Embodiment 33, wherein the resected tissue is infected tissue, necrotic tissue, or diseased tissue.

Embodiment 36. The method of Embodiment 33 or 34, wherein the subject is suspected of or diagnosed as having a cancer.

Embodiment 37. The method of Embodiment 36, wherein the cancer is breast cancer.

Embodiment 38. The method of Embodiment 33, wherein the subject is suspected of or diagnosed as having ductal carcinoma in situ.

Embodiment 39. The method of any one of Embodiments 33-38, wherein the analyte is RNA.

Embodiment 40. The method of Embodiment 39, wherein the RNA is mRNA.

Embodiment 41. The method of any one of Embodiments 33-38, wherein the analyte is DNA.

Embodiment 42. The method of Embodiment 41, wherein the DNA is genomic DNA.

Embodiment 43. The method of any one of Embodiments 33-42, wherein the array comprises a slide having the plurality of capture probes.

Embodiment 44. The method of any one of Embodiments 33-42, wherein the array is a bead array.

Embodiment 45. The method of any one of Embodiments 33-44, wherein step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof.

Embodiment 46. The method of Embodiment 45, wherein the sequencing is high throughput sequencing.

Embodiment 47. The method of any one of Embodiments 33-46, wherein step (b) comprises extending a 3' end of the capture probe using the specifically bound analyte as a template to generate an extended capture probe.

Embodiment 48. The method of Embodiment 47, wherein step (b) further comprises generating a single-stranded nucleic acid comprising a sequence that is complementary to all or a part of the extended capture probe.

Embodiment 49. A method of treating a subject in need thereof, the method comprising:

resecting tissue from the subject using a surgical margin previously determined using a method comprising the steps of:

(a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte;

(b) disposing the tissue sample onto an array, wherein the array comprises a plurality of capture probes, wherein a capture probe of the plurality of capture probes comprises a spatial barcode and a capture domain that binds specifically to the analyte capture sequence;

(c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;

(d) comparing the presence of the analyte at the location in the tissue sample to presence of the analyte at different location(s) in the tissue sample, and determining the surgical margin based on the comparison.

Embodiment 50. The method of Embodiment 49, wherein the resected tissue is a tumor.

Embodiment 51. The method of Embodiment 49, wherein the resected tissue is infected tissue, necrotic tissue, or diseased tissue.

Embodiment 52. The method of Embodiment 49 or 50, wherein the subject is suspected of or diagnosed as having a cancer.

Embodiment 53. The method of Embodiment 52, wherein the cancer is breast cancer.

Embodiment 54. The method of Embodiment 49, wherein the subject is suspected of or diagnosed as having ductal carcinoma in situ.

Embodiment 55. The method of any one of Embodiments 49-54, wherein the analyte is a protein.

Embodiment 56. The method of Embodiment 55, wherein the protein is an intracellular protein.

Embodiment 57. The method of Embodiment 55, wherein the protein is an extracellular protein.

Embodiment 58. The method of any one of Embodiments 55-57, wherein the analyte binding moiety is an antibody or an antigen-binding antibody fragment.

Embodiment 59. The method of any one of Embodiments 49-58, wherein the array comprises a slide having the plurality of capture probes.

Embodiment 60. The method of any one of Embodiments 49-58, wherein the array is a bead array.

Embodiment 61. The method of any one of Embodiments 49-60, wherein step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof.

Embodiment 62. The method of Embodiment 61, wherein the sequencing is high throughput sequencing.

Embodiment 63. The method of any one of Embodiments 49-62, wherein step (c) comprises extending a 3' end of the capture probe using the specifically bound analyte capture agent as a template to generate an extended capture probe.

Embodiment 64. The method of Embodiment 63, wherein step (c) further comprises generating a single-stranded nucleic acid comprising a sequence that is complementary to all or a part of the extended capture probe.

Embodiment 65. A method of identifying a surgical margin of a tissue to be resected in a subject, the method comprising:
  (a) contacting a tissue sample obtained from the subject to an array comprising a plurality of capture probes, wherein a capture probe of the plurality of capture probes comprises (i) a capture domain that specifically binds to an analyte of the tissue sample and (ii) a spatial barcode;
  (b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
  (c) comparing the presence of the analyte at the location in the tissue sample to presence of the analyte at different location(s) in the tissue sample, and determining the surgical margin of the tissue to be resected from the subject based on the comparison.

Embodiment 66. The method of Embodiment 65, wherein the tissue to be resected is a tumor.

Embodiment 67. The method of Embodiment 65, wherein the tissue to be resected is infected tissue, necrotic tissue, or diseased tissue.

Embodiment 68. The method of Embodiment 65 or 66, wherein the subject is suspected of or diagnosed as having a cancer.

Embodiment 69. The method of Embodiment 68, wherein the cancer is breast cancer.

Embodiment 70. The method of Embodiment 65, wherein the subject is suspected of or diagnosed as having ductal carcinoma in situ.

Embodiment 71. The method of any one of Embodiments 65-70, wherein the analyte is RNA.

Embodiment 72. The method of Embodiment 71, wherein the RNA is mRNA.

Embodiment 73. The method of any one of Embodiments 65-70, wherein the analyte is DNA.

Embodiment 74. The method of Embodiment 73, wherein the DNA is genomic DNA.

Embodiment 75. The method of any one of Embodiments 65-74, wherein the array comprises a slide.

Embodiment 76. The method of any one of Embodiments 65-74, wherein the array is a bead array.

Embodiment 77. The method of any one of Embodiments 65-76, wherein step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof.

Embodiment 78. The method of Embodiment 77, wherein the sequencing is high throughput sequencing.

Embodiment 79. The method of any one of Embodiments 65-78, wherein step (b) comprises extending a 3' end of the capture probe using the specifically bound analyte as a template to generate an extended capture probe.

Embodiment 80. The method of Embodiment 79, wherein step (b) further comprises generating a single-stranded nucleic acid comprising a sequence that is complementary to all or a part of the extended capture probe.

Embodiment 81. A method of identifying a surgical margin of a tissue to be resected in a subject, the method comprising:
  (a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte;
  (b) disposing the tissue sample onto an array, wherein the array comprises a plurality of capture probes, wherein a capture probe of the plurality of capture probes comprises a spatial barcode and a capture domain that binds specifically to the analyte capture sequence;
  (c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
  (d) comparing the presence of the analyte at the location in the tissue sample to presence of the analyte at different location(s) in the tissue sample, and determining the surgical margin of the tissue to be resected from the subject based on the comparison.

Embodiment 82. The method of Embodiment 81, wherein the tissue to be resected is a tumor.

Embodiment 83. The method of Embodiment 81, wherein the tissue to be resected is infected tissue, necrotic tissue, or diseased tissue.

Embodiment 84. The method of Embodiment 81 or 82, wherein the subject is suspected of or diagnosed as having a cancer.

Embodiment 85. The method of Embodiment 84, wherein the cancer is breast cancer.

Embodiment 86. The method of Embodiment 81, wherein the subject is suspected of or diagnosed as having ductal carcinoma in situ.

Embodiment 87. The method of any one of Embodiments 81-86, wherein the analyte is a protein.

Embodiment 88. The method of Embodiment 87, wherein the protein is an intracellular protein.

Embodiment 89. The method of Embodiment 87, wherein the protein is an extracellular protein.

Embodiment 90. The method of any one of Embodiments 87-89, wherein the analyte binding moiety is an antibody or an antigen-binding antibody fragment.

Embodiment 91. The method of any one of Embodiments 81-90, wherein the array comprises a slide.

Embodiment 92. The method of any one of Embodiments 81-90, wherein the array is a bead array.

Embodiment 93. The method of any one of Embodiments 81-92, wherein step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof.

Embodiment 94. The method of Embodiment 93, wherein the sequencing is high throughput sequencing.

Embodiment 95. The method of any one of Embodiments 81-94, wherein step (c) comprises extending a 3' end of the capture probe using the specifically bound analyte capture agent as a template to generate an extended capture probe.

Embodiment 96. The method of Embodiment 95, wherein step (c) further comprises generating a single-stranded nucleic acid comprising a sequence that is complementary to all or a part of the extended capture probe.

Embodiment 97. A method of reducing the risk of re-excision of a tissue from a subject, the method comprising:
resecting tissue from the subject using a surgical margin previously determined using a method comprising the steps of:
(a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode;
(b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
(c) comparing the presence of the analyte at the location in the tissue sample to presence of the analyte at different location(s) in the tissue sample, and determining the surgical margin based on the comparison.

Embodiment 98. The method of Embodiment 97, wherein the resected tissue is a tumor.

Embodiment 99. The method of Embodiment 97, wherein the resected tissue is infected tissue, necrotic tissue, or diseased tissue.

Embodiment 100. The method of Embodiment 97 or 98, wherein the subject is suspected of or diagnosed as having a cancer.

Embodiment 101. The method of Embodiment 100, wherein the cancer is breast cancer.

Embodiment 102. The method of Embodiment 97, wherein the subject is suspected of or diagnosed as having ductal carcinoma in situ.

Embodiment 103. The method of any one of Embodiments 97-102, wherein the analyte is RNA.

Embodiment 104. The method of Embodiment 103, wherein the RNA is mRNA.

Embodiment 105. The method of any one of Embodiments 97-102, wherein the analyte is DNA.

Embodiment 106. The method of Embodiment 105, wherein the DNA is genomic DNA.

Embodiment 107. The method of any one of Embodiments 97-106, wherein the array comprises a slide having the plurality of capture probes.

Embodiment 108. The method of any one of Embodiments 97-106, wherein the array is a bead array.

Embodiment 109. The method of any one of Embodiments 97-108, wherein step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof.

Embodiment 110. The method of Embodiment 109, wherein the sequencing is high throughput sequencing.

Embodiment 111. The method of any one of Embodiments 97-110, wherein step (b) comprises extending a 3' end of the capture probe using the specifically bound analyte as a template to generate an extended capture probe.

Embodiment 112. The method of Embodiment 111, wherein step (b) further comprises generating a single-stranded nucleic acid comprising a sequence that is complementary to all or a part of the extended capture probe.

Embodiment 113. A method of reducing the risk of re-excision of a tissue from a subject, the method comprising:
resecting tissue from the subject using a surgical margin previously determined using a method comprising the steps of:
(a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte;
(b) disposing the tissue sample onto an array, wherein the array comprises a plurality of capture probes, wherein a capture probe of the plurality of capture probes comprises a spatial barcode and a capture domain that binds specifically to the analyte capture sequence;
(c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
(d) comparing the presence of the analyte at the location in the tissue sample to presence of the analyte at different location(s) in the tissue sample, and determining the surgical margin based on the comparison.

Embodiment 114. The method of Embodiment 113, wherein the resected tissue is a tumor.

Embodiment 115. The method of Embodiment 113, wherein the resected tissue is infected tissue, necrotic tissue, or diseased tissue.

Embodiment 116. The method of Embodiment 113 or 114, wherein the subject is suspected of or diagnosed as having a cancer.

Embodiment 117. The method of Embodiment 116, wherein the cancer is breast cancer.

Embodiment 118. The method of Embodiment 113, wherein the subject is suspected of or diagnosed as having ductal carcinoma in situ.

Embodiment 119. The method of any one of Embodiments 113-118, wherein the analyte is a protein.

Embodiment 120. The method of Embodiment 119, wherein the protein is intracellular.

Embodiment 121. The method of Embodiment 119, wherein the protein is extracellular.

Embodiment 122. The method of any one of Embodiments 119-121, wherein the analyte binding moiety is an antibody or an antigen-binding antibody fragment.

Embodiment 123. The method of any one of Embodiments 113-122, wherein the array comprises a slide having the plurality of capture probes.

Embodiment 124. The method of any one of Embodiments 113-122, wherein the array is a bead array.

Embodiment 125. The method of any one of Embodiments 113-124, wherein step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof.

Embodiment 126. The method of Embodiment 125, wherein the sequencing is high throughput sequencing.

Embodiment 127. The method of any one of Embodiments 113-126, wherein step (c) comprises extending a 3' end of the capture probe using the specifically bound analyte capture agent as a template to generate an extended capture probe.

Embodiment 128. The method of Embodiment 127, wherein step (c) further comprises generating a single-stranded nucleic acid comprising a sequence that is complementary to all or a part of the extended capture probe.

Embodiment 129. A method of reducing the rate of recurrence of a tissue abnormality in a subject, the method comprising:
resecting tissue from the subject using a surgical margin previously determined using a method comprising the steps of:
(a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode;
(b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
(c) comparing the presence of the analyte at the location in the tissue sample to presence of the analyte at different location(s) in the tissue sample, and determining the surgical margin based on the comparison.

Embodiment 130. The method of Embodiment 129, wherein the resected tissue is a tumor.

Embodiment 131. The method of Embodiment 129, wherein the resected tissue is infected tissue, necrotic tissue, or diseased tissue.

Embodiment 132. The method of Embodiment 129 or 130, wherein the subject is suspected of or diagnosed as having a cancer.

Embodiment 133. The method of Embodiment 132, wherein the cancer is breast cancer.

Embodiment 134. The method of Embodiment 129, wherein the subject is suspected of or diagnosed as having ductal carcinoma in situ.

Embodiment 135. The method of any one of Embodiments 129-134, wherein the analyte is RNA.

Embodiment 136. The method of Embodiment 135, wherein the RNA is mRNA.

Embodiment 137. The method of any one of Embodiments 129-134, wherein the analyte is DNA.

Embodiment 138. The method of Embodiment 137, wherein the DNA is genomic DNA.

Embodiment 139. The method of any one of Embodiments 129-138, wherein the array comprises a slide having the plurality of capture probes.

Embodiment 140. The method of any one of Embodiments 129-138, wherein the array is a bead array.

Embodiment 141. The method of any one of Embodiments 129-140, wherein step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof.

Embodiment 142. The method of Embodiment 141, wherein the sequencing is high throughput sequencing.

Embodiment 143. The method of any one of Embodiments 129-142, wherein step (b) comprises extending a 3' end of the capture probe using the specifically bound analyte as a template to generate an extended capture probe.

Embodiment 144. The method of Embodiment 143, wherein step (b) further comprises generating a single-stranded nucleic acid comprising a sequence that is complementary to all or a part of the extended capture probe.

Embodiment 145. A method of reducing the rate of recurrence of a tissue abnormality in a subject, the method comprising:
resecting tissue from the subject using a surgical margin previously determined using a method comprising the steps of:
(a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte;
(b) disposing the tissue sample onto an array, wherein the array comprises a plurality of capture probes, wherein a capture probe of the plurality of capture probes comprises a spatial barcode and a capture domain that binds specifically to the analyte capture sequence;
(c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
(d) comparing the presence of the analyte at the location in the tissue sample to presence of the analyte at different location(s) in the tissue sample, and determining the surgical margin based on the comparison.

Embodiment 146. The method of Embodiment 145, wherein the resected tissue is a tumor.

Embodiment 147. The method of Embodiment 145, wherein the resected tissue is infected tissue, necrotic tissue, or diseased tissue.

Embodiment 148. The method of Embodiment 145 or 146, wherein the subject is suspected of or diagnosed as having a cancer.

Embodiment 149. The method of Embodiment 148, wherein the cancer is breast cancer.

Embodiment 150. The method of Embodiment 145, wherein the subject is suspected of or diagnosed as having ductal carcinoma in situ.

Embodiment 151. The method of any one of Embodiments 145-150, wherein the analyte is a protein.

Embodiment 152. The method of Embodiment 151, wherein the protein is an intracellular protein.

Embodiment 153. The method of Embodiment 151, wherein the protein is an extracellular protein.

Embodiment 154. The method of any one of Embodiments 151-153, wherein the analyte binding moiety is an antibody or an antigen-binding antibody fragment.

Embodiment 155. The method of any one of Embodiments 145-154, wherein the array comprises a slide having the plurality of capture probes.

Embodiment 156. The method of any one of Embodiments 145-154, wherein the array is a bead array.

Embodiment 157. The method of any one of Embodiments 145-156, wherein step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof.

Embodiment 158. The method of Embodiment 157, wherein the sequencing is high throughput sequencing.

Embodiment 159. The method of any one of Embodiments 145-158, wherein step (c) comprises extending a 3' end of the capture probe using the specifically bound analyte capture agent as a template to generate an extended capture probe.

Embodiment 160. The method of Embodiment 159, wherein step (c) further comprises generating a single-stranded nucleic acid comprising a sequence that is complementary to all or a part of the extended capture probe.

Embodiment 161. A method of treating a subject, the method comprising:
excising a nerve or blood vessel that is within a surgical margin in the subject, or avoiding excision of a nerve or blood vessel outside of the surgical margin in the subject, wherein the surgical margin was previously determined using a method comprising the steps of:
(a) contacting a tissue sample obtained from the subject to an array comprising a plurality of capture probes, wherein a capture probe of the plurality of capture probes comprises a (i) capture domain that specifically binds to an analyte of the tissue sample and (ii) a spatial barcode;
(b) determining (i) all or a part of a nucleic acid sequence corresponding to the analyte specifically bound to the capture domain or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
(c) comparing the presence of the analyte at the location in the tissue sample to presence of the analyte at different location(s) in the tissue sample, and determining the surgical margin based on the comparison.

Embodiment 162. The method of Embodiment 161, wherein the subject is suspected of or diagnosed as having a cancer.

Embodiment 163. The method of Embodiment 162, wherein the cancer is breast cancer.

Embodiment 164. The method of Embodiment 161, wherein the subject is suspected of or diagnosed as having ductal carcinoma in situ.

Embodiment 165. The method of any one of Embodiments 161-164, wherein the analyte is RNA.

Embodiment 166. The method of Embodiment 165, wherein the RNA is mRNA.

Embodiment 167. The method of any one of Embodiments 161-164, wherein the analyte is DNA.

Embodiment 168. The method of Embodiment 167, wherein the DNA is genomic DNA.

Embodiment 169. The method of any one of Embodiments 161-168, wherein the array comprises a slide having the plurality of capture probes.

Embodiment 170. The method of any one of Embodiments 161-169, wherein the array is a bead array.

Embodiment 171. The method of any one of Embodiments 161-170, wherein step (b) comprises sequencing (i) all or a part of the nucleic acid sequence corresponding to the analyte specifically bound to the capture domain or a complement thereof, and (ii) all or a part of the nucleic acid sequence corresponding to the spatial barcode or a complement thereof.

Embodiment 172. The method of Embodiment 171, wherein the sequencing is high throughput sequencing.

Embodiment 173. The method of any one of Embodiments 161-172, wherein step (b) comprises extending a 3' end of the capture probe using the specifically bound analyte as a template to generate an extended capture probe.

Embodiment 174. The method of Embodiment 173, wherein step (b) further comprises generating a single-stranded nucleic acid comprising a sequence that is complementary to all or a part of the extended capture probe.

Embodiment 175. The method of any one of Embodiments 161-174, wherein the method excising a nerve or blood vessel that is within the surgical margin in the subject.

Embodiment 176. The method of any one of Embodiments 161-174, wherein the method comprises avoiding excision of a nerve or blood vessel outside of the surgical margin in the subject.

Embodiment 177. A method of treating a subject, the method comprising:
excising a nerve or blood vessel that is within a surgical margin in the subject, or avoiding excision of a nerve or blood vessel outside of the surgical margin in the subject, wherein the surgical margin was previously determined using a method comprising the steps of:
(a) contacting a tissue sample obtained from the subject to a plurality of analyte capture agents, wherein an analyte capture agent of the plurality of analyte capture agents comprises an analyte binding moiety barcode, an analyte capture sequence, and an analyte binding moiety that binds specifically to an analyte;
(b) disposing the tissue sample onto an array, wherein the array comprises a plurality of capture probes, wherein a capture probe of the plurality of capture probes comprises a spatial barcode and a capture domain that binds specifically to the analyte capture sequence;
(c) determining (i) all or a part of a nucleic acid sequence corresponding to the analyte binding moiety barcode or a complement thereof, and (ii) all or a part of a nucleic acid sequence corresponding to the spatial barcode or a complement thereof, and using the determined nucleic acid sequences of (i) and (ii) to identify the presence of the analyte at a location in the tissue sample;
(d) comparing presence of the analyte at the location in the tissue sample to presence of the analyte at different location(s) in the tissue sample, and determining the surgical margin based on the comparison.

Embodiment 178. The method of Embodiment 177, wherein the subject is suspected of or diagnosed as having a cancer.

Embodiment 179. The method of Embodiment 178, wherein the cancer is breast cancer.

Embodiment 180. The method of Embodiment 177, wherein the subject is suspected of or diagnosed as having ductal carcinoma in situ.

Embodiment 181. The method of any one of Embodiments 177-180, wherein the analyte is a protein.

Embodiment 182. The method of Embodiment 181, wherein the protein is an intracellular protein.

Embodiment 183. The method of Embodiment 181, wherein the protein is an extracellular protein.

Embodiment 184. The method of any one of Embodiments 181-183, wherein the analyte binding moiety is an antibody or an antigen-binding antibody fragment.

Embodiment 185. The method of any one of Embodiments 177-184, wherein the array comprises a slide having the plurality of capture probes.

Embodiment 186. The method of any one of Embodiments 177-184, wherein the array is a bead array.

Embodiment 187. The method of any one of Embodiments 177-186, wherein step (c) comprises sequencing (i) all or a part of the nucleic acid sequence corresponding to the analyte binding moiety barcode or a complement thereof, and (ii) all or a part of the nucleic acid sequence corresponding to the spatial barcode or a complement thereof.

Embodiment 188. The method of Embodiment 187, wherein the sequencing is high throughput sequencing.

Embodiment 189. The method of any one of Embodiments 177-188, wherein step (c) comprises extending a 3' end of the capture probe using the specifically bound analyte capture agent as a template to generate an extended capture probe.

Embodiment 190. The method of Embodiment 189, wherein step (c) further comprises generating a single-stranded nucleic acid comprising a sequence that is complementary to all or a part of the extended capture probe.

Embodiment 191. The method of any one of Embodiments 177-190, wherein the method comprises excising a nerve or blood vessel that is within the surgical margin in the subject.

Embodiment 192. The method of any one of Embodiments 177-190, wherein the method comprises avoiding excision of a nerve or blood vessel outside of the surgical margin in the subject.

What is claimed is:

1. A method of determining a surgical margin of a tissue to be resected in a subject, the method comprising:
    (a) contacting a tissue section obtained from the subject to a substrate comprising a plurality of capture probes affixed to the substrate, wherein a capture probe of the plurality of capture probes comprises (i) a capture domain that hybridizes to an analyte of the tissue section and (ii) a spatial barcode;
    (b) permeabilizing the tissue section and hybridizing the analyte to the capture domain;
    (c) determining (i) all or a part of a nucleic acid sequence corresponding to the analyte hybridized to the capture domain or a complement thereof, and (ii) the spatial barcode or a complement thereof, and using the determined nucleic acid sequences of (i) and (ii) to identify the presence of the analyte at a location in the tissue section; and
    (d) comparing the presence of the analyte at the location in the tissue section to presence of the analyte at one or more different locations in the tissue section, and determining the surgical margin of the tissue to be resected from the subject based on the comparison.

2. The method of claim 1, wherein the presence of the analyte at the location in the tissue section is increased compared to the presence of the analyte at the different location in the tissue section.

3. The method of claim 1, wherein the presence of the analyte at the location in the tissue section is decreased compared to the presence of the analyte at the different location in the tissue section.

4. The method of claim 1, wherein the different locations in the tissue section are reference locations.

5. The method of claim 4, wherein the reference locations in the tissue section are locations of non-cancerous tissue and/or non-tumor tissue.

6. The method of claim 1, wherein the tissue to be resected is a tumor.

7. The method of claim 1, wherein the tissue to be resected is an infected tissue, a necrotic tissue, or a diseased tissue.

8. The method of claim 7, wherein the tissue to be resected is infected by a bacterium, a virus, a fungus, a parasite, and/or protozoa.

9. The method of claim 1, wherein the subject is suspected of or diagnosed as having a cancer.

10. The method of claim 9, wherein the cancer is breast cancer.

11. The method of claim 1, wherein the subject is suspected of or diagnosed as having ductal carcinoma in situ.

12. The method of claim 1, wherein the analyte is ribonucleic acid (RNA), deoxyribonucleic (DNA), or protein.

13. The method of claim 12, wherein the RNA is mRNA.

14. The method of claim 12, wherein the DNA is genomic DNA.

15. The method of claim 12, wherein the analyte is a tumor biomarker and/or a tumor antigen.

16. The method of claim 1, wherein the array is a bead array.

17. The method of claim 1, wherein step (c) comprises sequencing (i) all or a part of the nucleic acid sequence corresponding to the analyte specifically bound to the capture domain or a complement thereof, and (ii) the spatial barcode or a complement thereof.

18. The method of claim 17, wherein the sequencing is high throughput sequencing.

19. The method of claim 1, wherein step (c) comprises extending a 3' end of the capture probe using the hybridized analyte as a template to generate an extended capture probe.

20. The method of claim 19, wherein step (c) further comprises generating a single-stranded nucleic acid comprising a nucleic acid sequence that is complementary to all or a part of the extended capture probe.

21. The method of claim 1, wherein the capture probe further comprises one or more functional domains, a unique molecular identifier, a cleavage domain, and combinations thereof.

22. The method of claim 1, wherein the capture domain comprises a poly-uridine sequence or a poly-thymidine sequence.

23. The method of claim 1, wherein comparing the presence of the analyte at the location in the tissue section to the presence of the analyte at one or more different locations in the tissue section further comprises determining the size and site of the tissue to be resected from the subject.

24. The method of claim 1, wherein the method results in a:
    a) reduced rate of re-excision of the tissue; and/or
    b) reduced rate of recurrence of the tissue abnormality in the subject.

25. The method of claim 1, wherein the method further comprises treatment of the subject by surgery after step (d).

26. The method of claim 1, wherein the tissue section was obtained from the subject.

27. The method of claim 1, wherein the tissue section was previously fixed and/or stained.

28. The method of claim 27, wherein the tissue section was previously stained by hematoxylin and eosin, immunohistochemistry, and/or immunofluorescence.

* * * * *

UNITED STATES PATENT AND TRADEMARK OFFICE
CERTIFICATE OF CORRECTION

| | | |
|---|---|---|
| PATENT NO. | : 11,407,992 B2 | Page 1 of 1 |
| APPLICATION NO. | : 17/549175 | |
| DATED | : August 9, 2022 | |
| INVENTOR(S) | : Smritee Dadhwal | |

It is certified that error appears in the above-identified patent and that said Letters Patent is hereby corrected as shown below:

On the Title Page

Column 2, under item (56) U.S. Patent Documents, Line 15, delete "Homes" and insert -- Hornes --.

In the Claims

Column 68, Approximately Line 17, in Claim 12, delete "deoxyribonucleic" and insert
-- deoxyribonucleic acid --.

Signed and Sealed this
Fourth Day of October, 2022

Katherine Kelly Vidal
*Director of the United States Patent and Trademark Office*